(12) United States Patent
Medina-Ramirez et al.

(10) Patent No.: US 11,344,618 B2
(45) Date of Patent: May 31, 2022

(54) HIV ENVELOPE GLYCOPROTEIN IMMUNOGENS

(71) Applicant: Academisch Medisch Centrum, Amsterdam (NL)

(72) Inventors: Max Medina-Ramirez, Amsterdam (NL); Rogier Sanders, Amsterdam (NL)

(73) Assignee: Academisch Medisch Centrum, Amsterdam (NL)

( * ) Notice: Subject to any disclaimer, the term of this patent is extended or adjusted under 35 U.S.C. 154(b) by 280 days.

(21) Appl. No.: 16/642,131

(22) PCT Filed: Aug. 27, 2018

(86) PCT No.: PCT/EP2018/073053
§ 371 (c)(1),
(2) Date: Feb. 26, 2020

(87) PCT Pub. No.: WO2019/042950
PCT Pub. Date: Mar. 7, 2019

(65) Prior Publication Data
US 2020/0353069 A1    Nov. 12, 2020

(30) Foreign Application Priority Data
Aug. 26, 2017 (EP) .................... 17188050

(51) Int. Cl.
| | | |
|---|---|---|
| *A61K 39/21* | (2006.01) | |
| *A61K 39/00* | (2006.01) | |
| *A61K 39/12* | (2006.01) | |
| *C07K 14/005* | (2006.01) | |
| *C07K 14/16* | (2006.01) | |
| *C12N 7/00* | (2006.01) | |

(52) U.S. Cl.
CPC ............. *A61K 39/21* (2013.01); *C07K 14/005* (2013.01); *C12N 7/00* (2013.01); *C12N 2740/16122* (2013.01); *C12N 2740/16134* (2013.01)

(58) Field of Classification Search
CPC ........ C07K 14/005; C12N 2740/16122; C12N 2740/16222; A61P 31/18; A61K 2039/53
See application file for complete search history.

(56) References Cited

U.S. PATENT DOCUMENTS

| | | |
|---|---|---|
| 2014/0322269 A1 | 10/2014 | Huang et al. |
| 2016/0185825 A1 | 6/2016 | Huang et al. |
| 2017/0233441 A1 | 8/2017 | Kwong et al. |

FOREIGN PATENT DOCUMENTS

| | | |
|---|---|---|
| WO | 2013/056122 A1 | 4/2013 |
| WO | 2016/037154 A1 | 3/2016 |

OTHER PUBLICATIONS

Sliepen, K. et al., "Engineering and Characterization of a Fluorescent Native-Like HIV-1 Envelope Glycoprotein Trimer," Biomolecules, published Oct. 23, 2015, vol. 5, Issue No. 4, pp. 2919-2934.
International Search Report of the International Searching Authority for PCT/EP2018/073053 dated Jan. 3, 2019.

*Primary Examiner* — Barry A Chestnut
(74) *Attorney, Agent, or Firm* — McBee Moore & Vanik IP, LLC; Susan McBee; Chester Moore

(57) ABSTRACT

The invention relates to an isolated, recombinant or synthetic polypeptide comprising an Env polypeptide of an HIV virus, the Env polypeptide comprising at least the amino acid residues K275, D276 and R278, wherein said numbering is according to the HxB2 reference sequence having the amino acid sequence of SEQ ID NO: 1.

15 Claims, 5 Drawing Sheets
Specification includes a Sequence Listing.

| Residue / Env Variant | A199 | K275 | D276 | R278 | D386 | D462 | S471 |
|---|---|---|---|---|---|---|---|
| WT | | | | | | | |
| 1MUT | | | ● | | | | |
| 2MUT | | | ● | ● | | | |
| 2MUT+E275K* ← | | ● | ● | ● | | | |
| 6MUT | ● | | ● | ● | ● | ● | ● |
| 6MUT+E275K* | ● | ● | ● | ● | ● | ● | ● |

* Refers to a change E to K at position 275 relative to the HxB2 reference sequence.

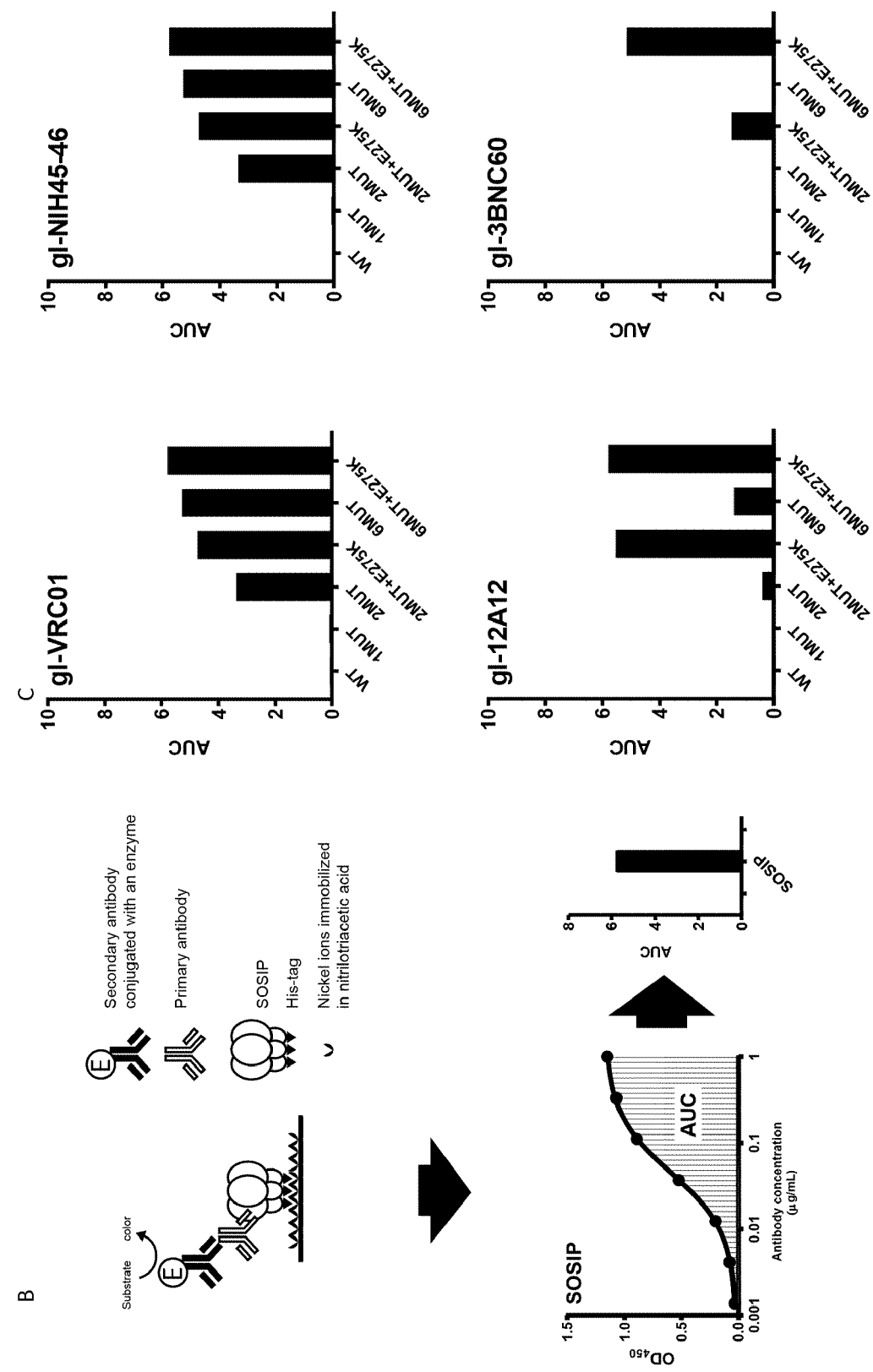
Figure 1B and C

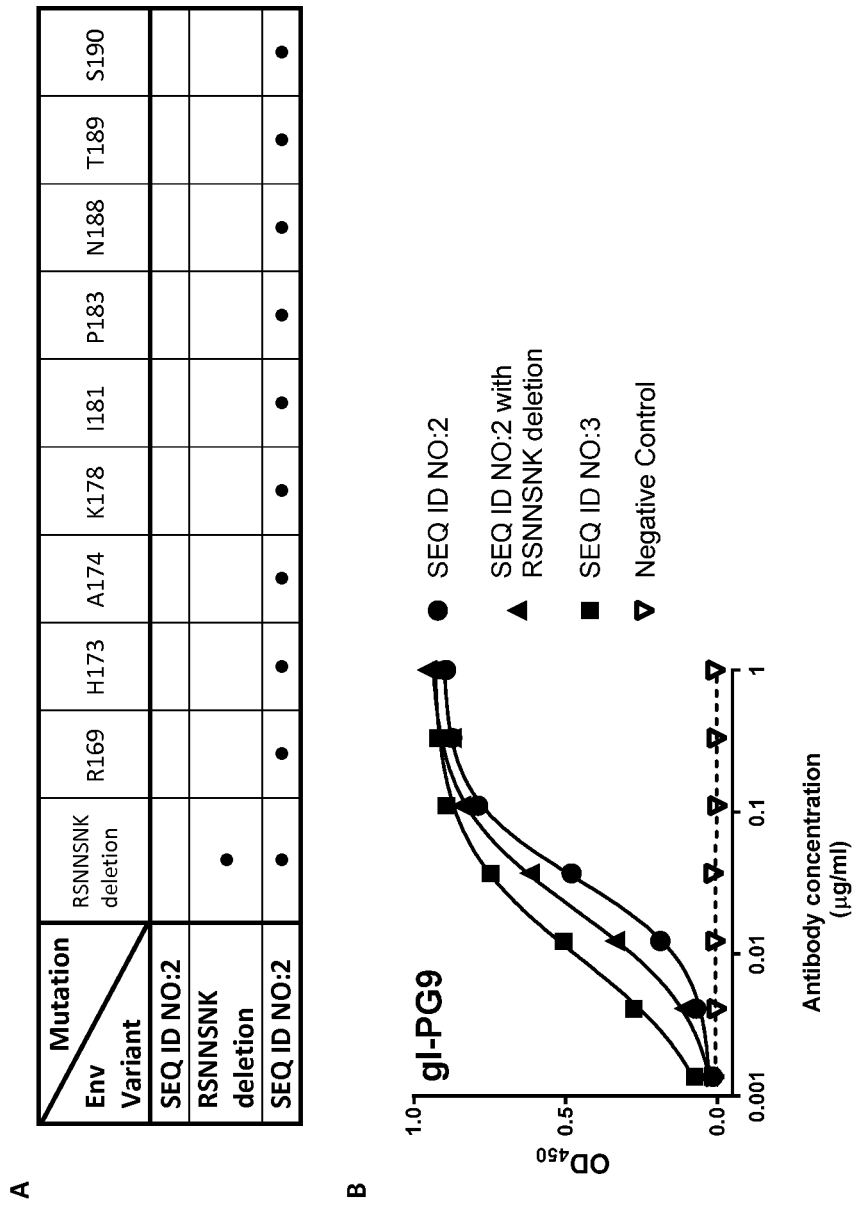

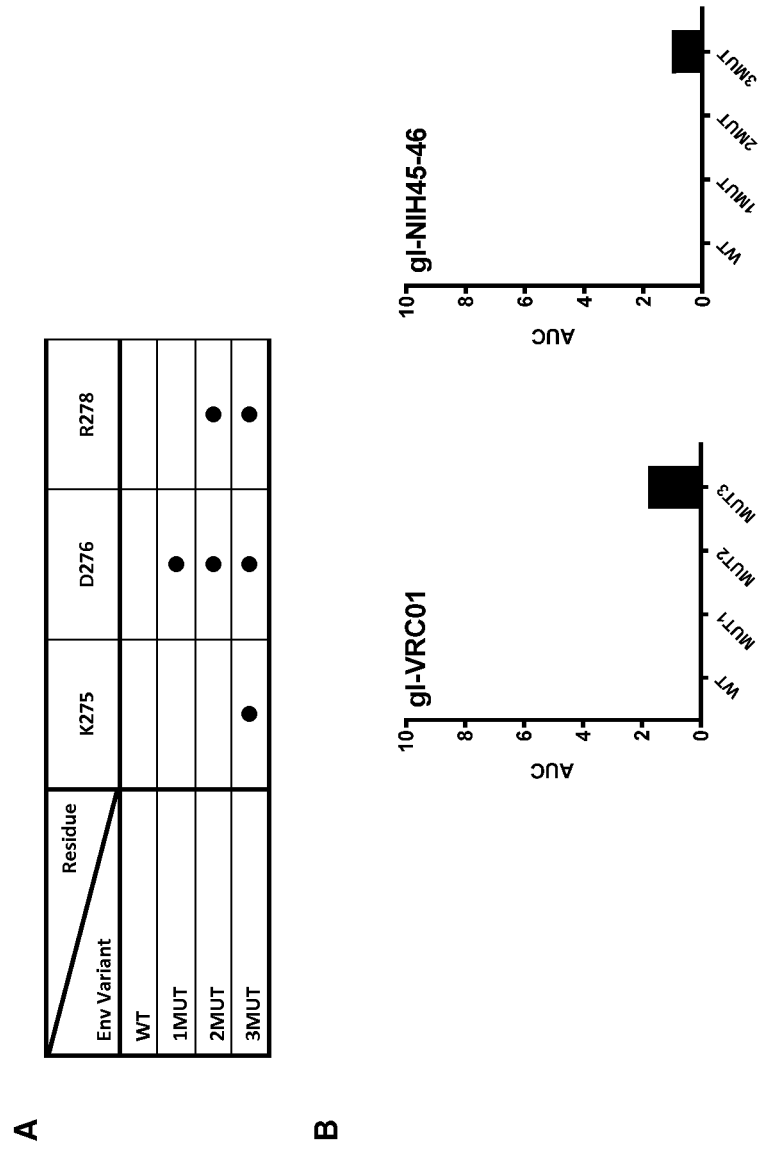
Fig. 3(A-B)

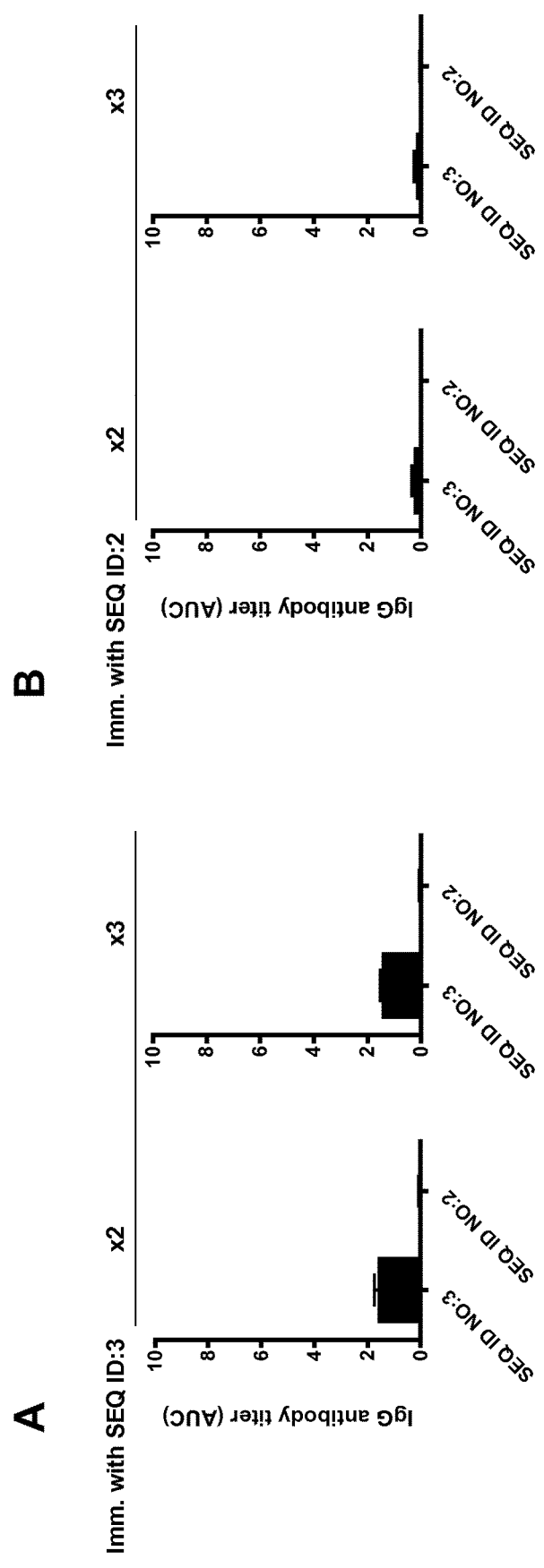
Figure 4(A and B)

SEQUENCE LISTING

```
<160> NUMBER OF SEQ ID NOS: 18

<210> SEQ ID NO 1
<211> LENGTH: 664
<212> TYPE: PRT
<213> ORGANISM: Artificial Sequence
<220> FEATURE:
<223> OTHER INFORMATION: HxB2

<400> SEQUENCE: 1

Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
            20                  25                  30

Lys Leu Trp Val Thr Val Tyr Tyr Gly Val Pro Val Trp Lys Glu Ala
        35                  40                  45

Thr Thr Thr Leu Phe Cys Ala Ser Asp Ala Lys Ala Tyr Asp Thr Glu
    50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
                85                  90                  95

Lys Asn Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Ser
        115                 120                 125

Leu Lys Cys Thr Asp Leu Lys Asn Asp Thr Asn Thr Asn Ser Ser Ser
    130                 135                 140

Gly Arg Met Ile Met Glu Lys Gly Glu Ile Lys Asn Cys Ser Phe Asn
145                 150                 155                 160

Ile Ser Thr Ser Ile Arg Gly Lys Val Gln Lys Glu Tyr Ala Phe Phe
                165                 170                 175

Tyr Lys Leu Asp Ile Ile Pro Ile Asp Asn Asp Thr Thr Ser Tyr Lys
            180                 185                 190

Leu Thr Ser Cys Asn Thr Ser Val Ile Thr Gln Ala Cys Pro Lys Val
        195                 200                 205

Ser Phe Glu Pro Ile Pro Ile His Tyr Cys Ala Pro Ala Gly Phe Ala
    210                 215                 220

Ile Leu Lys Cys Asn Asn Lys Thr Phe Asn Gly Thr Gly Pro Cys Thr
225                 230                 235                 240

Asn Val Ser Thr Val Gln Cys Thr His Gly Ile Arg Pro Val Val Ser
                245                 250                 255
```

```
Thr Gln Leu Leu Leu Asn Gly Ser Leu Ala Glu Glu Val Val Ile
            260                 265                 270
Arg Ser Val Asn Phe Thr Asp Asn Ala Lys Thr Ile Ile Val Gln Leu
        275                 280                 285
Asn Thr Ser Val Glu Ile Asn Cys Thr Arg Pro Asn Asn Asn Thr Arg
    290                 295                 300
Lys Arg Ile Arg Ile Gln Arg Gly Pro Gly Arg Ala Phe Val Thr Ile
305                 310                 315                 320
Gly Lys Ile Gly Asn Met Arg Gln Ala His Cys Asn Ile Ser Arg Ala
                325                 330                 335
Lys Trp Asn Asn Thr Leu Lys Gln Ile Ala Ser Lys Leu Arg Glu Gln
            340                 345                 350
Phe Gly Asn Asn Lys Thr Ile Ile Phe Lys Gln Ser Ser Gly Gly Asp
        355                 360                 365
Pro Glu Ile Val Thr His Ser Phe Asn Cys Gly Gly Glu Phe Phe Tyr
    370                 375                 380
Cys Asn Ser Thr Gln Leu Phe Asn Ser Thr Trp Phe Asn Ser Thr Trp
385                 390                 395                 400
Ser Thr Glu Gly Ser Asn Asn Thr Glu Gly Ser Asp Thr Ile Thr Leu
                405                 410                 415
Pro Cys Arg Ile Lys Gln Ile Ile Asn Met Trp Gln Lys Val Gly Lys
            420                 425                 430
Ala Met Tyr Ala Pro Pro Ile Ser Gly Gln Ile Arg Cys Ser Ser Asn
        435                 440                 445
Ile Thr Gly Leu Leu Leu Thr Arg Asp Gly Gly Asn Ser Asn Asn Glu
    450                 455                 460
Ser Glu Ile Phe Arg Pro Gly Gly Gly Asp Met Arg Asp Asn Trp Arg
465                 470                 475                 480
Ser Glu Leu Tyr Lys Tyr Lys Val Val Lys Ile Glu Pro Leu Gly Val
                485                 490                 495
Ala Pro Thr Lys Ala Lys Arg Arg Val Val Gln Arg Glu Lys Arg Ala
            500                 505                 510
Val Gly Ile Gly Ala Leu Phe Leu Gly Phe Leu Gly Ala Ala Gly Ser
        515                 520                 525
Thr Met Gly Ala Ala Ser Met Thr Leu Thr Val Gln Ala Arg Gln Leu
    530                 535                 540
Leu Ser Gly Ile Val Gln Gln Gln Asn Asn Leu Leu Arg Ala Ile Glu
545                 550                 555                 560
Ala Gln Gln His Leu Leu Gln Leu Thr Val Trp Gly Ile Lys Gln Leu
                565                 570                 575
Gln Ala Arg Ile Leu Ala Val Glu Arg Tyr Leu Lys Asp Gln Gln Leu
            580                 585                 590
Leu Gly Ile Trp Gly Cys Ser Gly Lys Leu Ile Cys Thr Thr Ala Val
        595                 600                 605
Pro Trp Asn Ala Ser Trp Ser Asn Lys Ser Leu Glu Gln Ile Trp Asn
    610                 615                 620
His Thr Thr Trp Met Glu Trp Asp Arg Glu Ile Asn Asn Tyr Thr Ser
625                 630                 635                 640
Leu Ile His Ser Leu Ile Glu Glu Ser Gln Asn Gln Gln Glu Lys Asn
                645                 650                 655
Glu Gln Glu Leu Leu Glu Leu Asp
            660
```

<210> SEQ ID NO 2
<211> LENGTH: 634
<212> TYPE: PRT
<213> ORGANISM: Artificial Sequence
<220> FEATURE:
<223> OTHER INFORMATION: BG505 SOSIP.v4.1

<400> SEQUENCE: 2

```
Ala Glu Asn Leu Trp Val Thr Val Tyr Tyr Gly Val Pro Val Trp Lys
1               5                   10                  15

Asp Ala Glu Thr Thr Leu Phe Cys Ala Ser Asp Ala Lys Ala Tyr Glu
            20                  25                  30

Thr Lys Lys His Asn Val Trp Ala Thr His Ala Cys Val Pro Thr Asp
        35                  40                  45

Pro Asn Pro Gln Glu Ile His Leu Glu Asn Val Thr Glu Glu Phe Asn
    50                  55                  60

Met Trp Lys Asn Asn Met Val Glu Gln Met His Thr Asp Ile Ile Ser
65                  70                  75                  80

Leu Trp Asp Gln Ser Leu Lys Pro Cys Val Lys Leu Thr Pro Leu Cys
                85                  90                  95

Val Thr Leu Gln Cys Thr Asn Val Thr Asn Asn Ile Thr Asp Asp Met
            100                 105                 110

Arg Gly Glu Leu Lys Asn Cys Ser Phe Asn Met Thr Thr Glu Leu Arg
        115                 120                 125

Asp Lys Lys Gln Lys Val Tyr Ser Leu Phe Tyr Arg Leu Asp Val Val
    130                 135                 140

Gln Ile Asn Glu Asn Gln Gly Asn Arg Ser Asn Asn Ser Asn Lys Glu
145                 150                 155                 160

Tyr Arg Leu Ile Asn Cys Asn Thr Ser Ala Ile Thr Gln Ala Cys Pro
                165                 170                 175

Lys Val Ser Phe Glu Pro Ile Pro Ile His Tyr Cys Ala Pro Ala Gly
            180                 185                 190

Phe Ala Ile Leu Lys Cys Lys Asp Lys Lys Phe Asn Gly Thr Gly Pro
        195                 200                 205

Cys Pro Ser Val Ser Thr Val Gln Cys Thr His Gly Ile Lys Pro Val
    210                 215                 220

Val Ser Thr Gln Leu Leu Leu Asn Gly Ser Leu Ala Glu Glu Glu Val
225                 230                 235                 240

Met Ile Arg Ser Glu Asn Ile Thr Asn Asn Ala Lys Asn Ile Leu Val
                245                 250                 255

Gln Phe Asn Thr Pro Val Gln Ile Asn Cys Thr Arg Pro Asn Asn Asn
            260                 265                 270

Thr Arg Lys Ser Ile Arg Ile Gly Pro Gly Gln Trp Phe Tyr Ala Thr
        275                 280                 285

Gly Asp Ile Ile Gly Asp Ile Arg Gln Ala His Cys Asn Val Ser Lys
    290                 295                 300

Ala Thr Trp Asn Glu Thr Leu Gly Lys Val Val Lys Gln Leu Arg Lys
305                 310                 315                 320

His Phe Gly Asn Asn Thr Ile Ile Arg Phe Ala Asn Ser Ser Gly Gly
                325                 330                 335

Asp Leu Glu Val Thr Thr His Ser Phe Asn Cys Gly Gly Glu Phe Phe
            340                 345                 350

Tyr Cys Asn Thr Ser Gly Leu Phe Asn Ser Thr Trp Ile Ser Asn Thr
        355                 360                 365

Ser Val Gln Gly Ser Asn Ser Thr Gly Ser Asn Asp Ser Ile Thr Leu
```

```
                    370                 375                 380
Pro Cys Arg Ile Lys Gln Ile Ile Asn Met Trp Gln Arg Ile Gly Gln
385                 390                 395                 400

Ala Met Tyr Ala Pro Pro Ile Gln Gly Val Ile Arg Cys Val Ser Asn
                405                 410                 415

Ile Thr Gly Leu Ile Leu Thr Arg Asp Gly Gly Ser Thr Asn Ser Thr
                420                 425                 430

Thr Glu Thr Phe Arg Pro Gly Gly Gly Asp Met Arg Asp Asn Trp Arg
            435                 440                 445

Ser Glu Leu Tyr Lys Tyr Lys Val Val Lys Ile Glu Pro Leu Gly Val
        450                 455                 460

Ala Pro Thr Arg Cys Lys Arg Arg Val Val Gly Arg Arg Arg Arg Arg
465                 470                 475                 480

Arg Ala Val Gly Ile Gly Ala Val Phe Leu Gly Phe Leu Gly Ala Ala
                485                 490                 495

Gly Ser Thr Met Gly Ala Ala Ser Met Thr Leu Thr Val Gln Ala Arg
                500                 505                 510

Asn Leu Leu Ser Gly Ile Val Gln Gln Gln Ser Asn Leu Leu Arg Ala
            515                 520                 525

Pro Glu Ala Gln Gln His Leu Leu Lys Leu Thr Val Trp Gly Ile Lys
        530                 535                 540

Gln Leu Gln Ala Arg Val Leu Ala Val Glu Arg Tyr Leu Arg Asp Gln
545                 550                 555                 560

Gln Leu Leu Gly Ile Trp Gly Cys Ser Gly Lys Leu Ile Cys Cys Thr
                565                 570                 575

Asn Val Pro Trp Asn Ser Ser Trp Ser Asn Arg Asn Leu Ser Glu Ile
                580                 585                 590

Trp Asp Asn Met Thr Trp Leu Gln Trp Asp Lys Glu Ile Ser Asn Tyr
            595                 600                 605

Thr Gln Ile Ile Tyr Gly Leu Leu Glu Glu Ser Gln Asn Gln Gln Glu
        610                 615                 620

Lys Asn Glu Gln Asp Leu Leu Ala Leu Asp
625                 630

<210> SEQ ID NO 3
<211> LENGTH: 627
<212> TYPE: PRT
<213> ORGANISM: Artificial Sequence
<220> FEATURE:
<223> OTHER INFORMATION: BG505 SOSIP.v4.1-GT1

<400> SEQUENCE: 3

Ala Glu Asn Leu Trp Val Thr Val Tyr Tyr Gly Val Pro Val Trp Lys
1               5                   10                  15

Asp Ala Glu Thr Thr Leu Phe Cys Ala Ser Asp Ala Lys Ala Tyr Glu
            20                  25                  30

Thr Lys Lys His Asn Val Trp Ala Thr His Ala Cys Val Pro Thr Asp
        35                  40                  45

Pro Asn Pro Gln Glu Ile His Leu Glu Asn Val Thr Glu Glu Phe Asn
    50                  55                  60

Met Trp Lys Asn Asn Met Val Glu Gln Met His Thr Asp Ile Ile Ser
65                  70                  75                  80

Leu Trp Asp Gln Ser Leu Lys Pro Cys Val Lys Leu Thr Pro Leu Cys
                85                  90                  95

Val Thr Leu Gln Cys Thr Asn Val Thr Asn Asn Ile Thr Asp Asp Met
```

```
            100                 105                 110
Arg Gly Glu Leu Lys Asn Cys Ser Phe Asn Met Thr Thr Glu Leu Arg
            115                 120                 125

Asp Lys Arg Gln Lys Val His Ala Leu Phe Tyr Lys Leu Asp Ile Val
            130                 135                 140

Pro Ile Asn Glu Asn Gln Asn Thr Ser Tyr Arg Leu Ile Asn Cys Asn
145                 150                 155                 160

Thr Ala Ala Ile Thr Gln Ala Cys Pro Lys Val Ser Phe Glu Pro Ile
                165                 170                 175

Pro Ile His Tyr Cys Ala Pro Ala Gly Phe Ala Ile Leu Lys Cys Lys
                180                 185                 190

Asp Lys Lys Phe Asn Gly Thr Gly Pro Cys Pro Ser Val Ser Thr Val
                195                 200                 205

Gln Cys Thr His Gly Ile Lys Pro Val Val Ser Thr Gln Leu Leu Leu
            210                 215                 220

Asn Gly Ser Leu Ala Glu Glu Val Met Ile Arg Ser Lys Asp Ile
225                 230                 235                 240

Arg Asn Asn Ala Lys Asn Ile Leu Val Gln Phe Asn Thr Pro Val Gln
                245                 250                 255

Ile Asn Cys Thr Arg Pro Asn Asn Asn Thr Arg Lys Ser Ile Arg Ile
                260                 265                 270

Gly Pro Gly Gln Trp Phe Tyr Ala Thr Gly Asp Ile Ile Gly Asp Ile
            275                 280                 285

Arg Gln Ala His Cys Asn Val Ser Lys Ala Thr Trp Asn Glu Thr Leu
            290                 295                 300

Gly Lys Val Val Lys Gln Leu Arg Lys His Phe Gly Asn Asn Thr Ile
305                 310                 315                 320

Ile Arg Phe Ala Asn Ser Ser Gly Gly Asp Leu Glu Val Thr Thr His
                325                 330                 335

Ser Phe Asn Cys Gly Gly Glu Phe Phe Tyr Cys Asp Thr Ser Gly Leu
                340                 345                 350

Phe Asn Ser Thr Trp Ile Ser Asn Thr Ser Val Gln Gly Ser Asn Ser
            355                 360                 365

Thr Gly Ser Asn Asp Ser Ile Thr Leu Pro Cys Arg Ile Lys Gln Ile
            370                 375                 380

Ile Asn Met Trp Gln Arg Ile Gly Gln Ala Met Tyr Ala Pro Pro Ile
385                 390                 395                 400

Gln Gly Val Ile Arg Cys Val Ser Asn Ile Thr Gly Leu Ile Leu Thr
                405                 410                 415

Arg Asp Gly Gly Ser Thr Asp Ser Thr Thr Glu Thr Phe Arg Pro Ser
                420                 425                 430

Gly Gly Asp Met Arg Asp Asn Trp Arg Ser Glu Leu Tyr Lys Tyr Lys
            435                 440                 445

Val Val Lys Ile Glu Pro Leu Gly Val Ala Pro Thr Arg Cys Lys Arg
450                 455                 460

Arg Val Val Gly Arg Arg Arg Arg Ala Val Gly Ile Gly Ala
465                 470                 475                 480

Val Phe Leu Gly Phe Leu Gly Ala Ala Gly Ser Thr Met Gly Ala Ala
                485                 490                 495

Ser Met Thr Leu Thr Val Gln Ala Arg Asn Leu Leu Ser Gly Ile Val
                500                 505                 510

Gln Gln Gln Ser Asn Leu Leu Arg Ala Pro Glu Ala Gln Gln His Leu
            515                 520                 525
```

```
Leu Lys Leu Thr Val Trp Gly Ile Lys Gln Leu Gln Ala Arg Val Leu
    530                 535                 540

Ala Val Glu Arg Tyr Leu Arg Asp Gln Gln Leu Leu Gly Ile Trp Gly
545                 550                 555                 560

Cys Ser Gly Lys Leu Ile Cys Cys Thr Asn Val Pro Trp Asn Ser Ser
                565                 570                 575

Trp Ser Asn Arg Asn Leu Ser Glu Ile Trp Asp Asn Met Thr Trp Leu
                580                 585                 590

Gln Trp Asp Lys Glu Ile Ser Asn Tyr Thr Gln Ile Ile Tyr Gly Leu
                595                 600                 605

Leu Glu Glu Ser Gln Asn Gln Gln Glu Lys Asn Glu Gln Asp Leu Leu
    610                 615                 620

Ala Leu Asp
625

<210> SEQ ID NO 4
<211> LENGTH: 41
<212> TYPE: DNA
<213> ORGANISM: Artificial Sequence
<220> FEATURE:
<223> OTHER INFORMATION: forward primer

<400> SEQUENCE: 4
atcaatgaaa accaggggaa tgagtacagg ctgatcaatt g                41

<210> SEQ ID NO 5
<211> LENGTH: 41
<212> TYPE: DNA
<213> ORGANISM: Artificial Sequence
<220> FEATURE:
<223> OTHER INFORMATION: reverse primer

<400> SEQUENCE: 5
caattgatca gcctgtactc attcccctgg ttttcattga t                41

<210> SEQ ID NO 6
<211> LENGTH: 16
<212> TYPE: PRT
<213> ORGANISM: Artificial Sequence
<220> FEATURE:
<223> OTHER INFORMATION: His-tag sequence

<400> SEQUENCE: 6

Gly Ser Gly Ser Gly Gly Ser Gly His His His His His His
1               5                   10                  15

<210> SEQ ID NO 7
<211> LENGTH: 7
<212> TYPE: PRT
<213> ORGANISM: Artificial Sequence
<220> FEATURE:
<223> OTHER INFORMATION: deletion

<400> SEQUENCE: 7

Arg Ser Asn Asn Ser Asn Lys
1               5

<210> SEQ ID NO 8
<211> LENGTH: 19
<212> TYPE: PRT
<213> ORGANISM: Artificial Sequence
<220> FEATURE:
<223> OTHER INFORMATION: example upper
```

```
<400> SEQUENCE: 8

Leu Leu Leu Thr Arg Asp Gly Gly Asn Ser Asn Asn Glu Ser Glu Ile
1               5                   10                  15

Phe Arg Pro

<210> SEQ ID NO 9
<211> LENGTH: 21
<212> TYPE: PRT
<213> ORGANISM: Artificial Sequence
<220> FEATURE:
<223> OTHER INFORMATION: example lower

<400> SEQUENCE: 9

Leu Leu Leu Thr Arg Asp Gly Gly Ser Asn Arg Ser Glu Pro Glu Val
1               5                   10                  15

Glu Ile Phe Arg Pro
            20

<210> SEQ ID NO 10
<211> LENGTH: 9
<212> TYPE: PRT
<213> ORGANISM: Artificial Sequence
<220> FEATURE:
<223> OTHER INFORMATION: deletion 434-442

<400> SEQUENCE: 10

Ile Asn Met Trp Gln Lys Val Gly Lys
1               5

<210> SEQ ID NO 11
<211> LENGTH: 10
<212> TYPE: PRT
<213> ORGANISM: Artificial Sequence
<220> FEATURE:
<223> OTHER INFORMATION: deletion 434-443

<400> SEQUENCE: 11

Ile Asn Met Trp Gln Lys Val Gly Lys Ala
1               5                   10

<210> SEQ ID NO 12
<211> LENGTH: 11
<212> TYPE: PRT
<213> ORGANISM: Artificial Sequence
<220> FEATURE:
<223> OTHER INFORMATION: deletion 434-444

<400> SEQUENCE: 12

Ile Asn Met Trp Gln Lys Val Gly Lys Ala Met
1               5                   10

<210> SEQ ID NO 13
<211> LENGTH: 14
<212> TYPE: PRT
<213> ORGANISM: Artificial Sequence
<220> FEATURE:
<223> OTHER INFORMATION: deletion 429-442

<400> SEQUENCE: 13

Arg Ile Lys Gln Ile Ile Asn Met Trp Gln Lys Val Gly Lys
1               5                   10

<210> SEQ ID NO 14
<211> LENGTH: 13
```

```
<212> TYPE: PRT
<213> ORGANISM: Artificial Sequence
<220> FEATURE:
<223> OTHER INFORMATION: deletion 430-442

<400> SEQUENCE: 14

Ile Lys Gln Ile Ile Asn Met Trp Gln Lys Val Gly Lys
1               5                   10

<210> SEQ ID NO 15
<211> LENGTH: 12
<212> TYPE: PRT
<213> ORGANISM: Artificial Sequence
<220> FEATURE:
<223> OTHER INFORMATION: deletion 431-442

<400> SEQUENCE: 15

Lys Gln Ile Ile Asn Met Trp Gln Lys Val Gly Lys
1               5                   10

<210> SEQ ID NO 16
<211> LENGTH: 11
<212> TYPE: PRT
<213> ORGANISM: Artificial Sequence
<220> FEATURE:
<223> OTHER INFORMATION: deletion 422-442

<400> SEQUENCE: 16

Gln Ile Ile Asn Met Trp Gln Lys Val Gly Lys
1               5                   10

<210> SEQ ID NO 17
<211> LENGTH: 10
<212> TYPE: PRT
<213> ORGANISM: Artificial Sequence
<220> FEATURE:
<223> OTHER INFORMATION: deletion 433-442

<400> SEQUENCE: 17

Ile Ile Asn Met Trp Gln Lys Val Gly Lys
1               5                   10

<210> SEQ ID NO 18
<211> LENGTH: 7
<212> TYPE: PRT
<213> ORGANISM: Artificial Sequence
<220> FEATURE:
<223> OTHER INFORMATION: linker

<400> SEQUENCE: 18

Asn Gly Thr Gly Gly Ser Gly
1               5
```

HIV ENVELOPE GLYCOPROTEIN IMMUNOGENS

TECHNICAL FIELD

The invention relates generally to novel HIV envelope proteins and to methods, compositions and products related thereto. More particularly, the invention relates to methods and compositions for the preparation, production, and administration of isolated novel HIV envelope nucleic acid and protein sequences suitable, for example, as vaccines against HIV.

BACKGROUND

An effective HIV vaccine requires the elicitation of protective titers of broadly neutralizing antibodies (bNAbs). The envelope glycoprotein (Env) on the virion surface is the only relevant target for bNAbs and, hence, is the main focus for antibody-based vaccine strategies. Approximately 30-50% of infected individuals eventually develop bNAbs, and passive immunization studies have shown that various bNAbs can protect macaques from experimental challenge. However, it has not yet been possible to induce bNAbs by vaccination.

The Env spike on HIV-1 virions is a metastable complex consisting of three gp120 and three gp41 subunits associated through non-covalent interactions. Soluble trimers of the SOSIP design that faithfully mimic the native spike have yielded valuable insights into the structural details of how Env functions and the bNAb epitopes it presents. SOSIP trimers have induced strong and consistent autologous Tier 2 NAb responses in rabbits and somewhat weaker responses in macaques. A major goal is now to devise a strategy to broaden these narrow specificity NAb responses into ones resembling bNAbs. To develop more sophisticated vaccination regimens will require combining our increasing knowledge of Env structure with an understanding of bNAb development.

During HIV-1 infection, bNAbs usually emerge over time from an initial, narrowly focused, autologous NAb response to transmitted/founder viruses. This process requires the specific activation of germline bNAb-precursors followed by the incorporation of high levels of somatic mutation mediated by multiple cycles of viral escape from antibody pressure generating new variants that, in turn, drive additional antibody affinity maturation. Currently, any bNAb sequence can be reverted to its corresponding germline precursor (germline-reverted) and used to study activation capacity of Env immunogens.

A bNAb epitope cluster of interest is the CD4-binding site (CD4bs). The CD4 receptor and several sub-families of bNAbs bind to overlapping epitopes on both gp120 monomers and native-like trimers. However, many antibodies that recognize CD4bs-associated epitopes on the outer domain (OD) of the gp120 monomer cannot do so on the trimer, due to topological constraints imposed by the trimeric architecture. This subset of CD4bs antibodies is non-neutralizing (i.e., non-NAbs) for Tier-2 viruses (Chen et al., 2009).

Recombinant Env (rEnv) immunogens are poorly recognized by germline-reverted (gl) bNAbs (gl-bNAbs) either when these antibodies are tested as soluble probes or as membrane-bound B cell receptors (BCRs). Some native-like trimers, including BG505 SOSIP.664, can engage trimer-apex gl-bNAbs (Sliepen et al., 2015), providing a strong foundation for structure-guided design improvements to yield higher affinity immunogens. It is an objective of the invention to provide HIV envelope glycoprotein (Env) immunogens with improved capacity for binding gl-bNAbs that target the trimer-apex and/or the CD4bs epitopes, that can bind gl-bNAbs with high affinity in vitro and/or, by extension, activate the analogous naïve B cells in vivo.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "Sequence_Listing_2924400-014000_ST25.txt" created on Jun. 18, 2021 and 20,246 bytes in size) is submitted concurrently with the instant application, and the entire contents of the Sequence Listing are incorporated herein by reference.

BRIEF DESCRIPTION OF THE FIGURES

FIG. 1 shows the in vitro binding of prototypical germline-VRC01-class antibodies to BG505 SOSIP.v4.1 variants.

FIG. 1A shows each specific residue or combination of residues introduced in variants of the Env protein.

FIG. 1B shows an overview of the capture ELISA scheme, designed to determine the binding properties of trimers of different Env polypeptides to antibodies. Nickel-nitrilotriacetic acid complexes (Ni-NTA) (pie shape) are immobilized in micro-well plates. The Ni-NTA complexes strongly interacts with the poly-histidine (His×8) tag at the C-terminus of the SOSIP sequence or any Env sequence (shown as black upside down triangles). This interaction specifically captures the trimers oriented upwards. Gradual concentrations of primary antibody (shown in white with black borders) are then added. Interaction between the primary antibody and the antigen is then allowed and after an incubation period the excess of primary antibody is washed away. A specific anti-primary antibody known as secondary antibody (shown in black) is then added and allowed to bind. After an incubation period the excess of secondary antibody is washed away and a substrate is added to allow development of color by a catalytic enzyme conjugated to the secondary antibody. The intensity of the color can be measured by spectrophotometry and the area under the curve is calculated and plotted. FIG. 1C shows area under the curve analysis from ELISA binding curves generated using a panel of germline antibodies derived from four representative bNAbs gl-VRC01, gl-NIH45-46, gl-12A12 and gl-3BNC60 from the VRC01-class. The dilution factor for all antibodies was 1:3. Area under the curve for each condition was calculated and the values were plotted as bars. The arrow indicated the minimal combination of mutations required to have a broad effect.

FIG. 2A shows each specific residue or combination of residues introduced in variants of the Env protein.

FIG. 2B shows representative ELISA binding which curves were generated using gl-PG9. The dilution factor for the antibody was 1:3.

FIG. 3A shows each specific residue or combination of residues introduced in variants of the Env protein derived from a clade B HIV virus named AMC008. FIG. 3B shows the area under the curve analysis from ELISA binding curves generated using a panel of germline antibodies derived from two representative bNAbs gl-VRC01 and gl-NIH45-46 from the VRC01-class. The dilution factor for both antibodies was 1:3. Area under the curve for each condition was calculated and the values were plotted as bars.

FIG. 4 shows the antibody binding titers in sera from the VH1-2/JH2/LC chimeric mouse model immunized three times with SEQ ID NO:2 or SEQ ID NO:3. Animals were immunized three time with SEQ ID NO:3 (A) or SEQ ID NO:2 (B). Sera post-immunization 2 and 3 were titrated against the indicated trimers (Y axis) by ELISA and processed as follows: the sera were serially diluted in three-fold steps, starting from a 1:100 dilution. The representative ELISA binding curves were used to calculate the area under the curve (AUC) and plotted as bars.

SUMMARY OF THE INVENTION

The invention is based on the finding that surprising identification of certain residues introduced in the Env protein of HIV which were capable of activating B-cell lines expressing the germline version of VRC01. The inventors tested four representative gl-bNAbs from the VRC01 class, and found that all had gl-VRC01-class binding properties if the Env proteins comprised residues K275, D276 and R278. The combination of these 3 residues is required, as residues D276 and R278 alone or in combination were unable to achieve broadly binding antibody activity in gl-12A12 and gl-3BNC60. It was therefore concluded that these residues are essential to achieve broadly binding antibody activity. This is illustrated in FIG. 1C.

Furthermore, when the residue D276 or the combination of D276 and R278 were introduced in a clade B-based Env protein, binding of two gl-VRC01-class antibodies was not observed. However, the presence of these 2 residues in combination with the residue K275, allowed binding of the antibodies gl-VRC01 and gl-NIH45-46. It was therefore concluded that these residues are essential to achieve gl-VRC01 class binding for Env proteins not only in the context of SOSIP Env proteins such as the SEQ ID NO:2, but also in other Env proteins, such as from a clade B HIV virus. This is illustrated in FIG. 3B.

Therefore, the invention provides an isolated, recombinant or synthetic polypeptide comprising an Env polypeptide of an HIV virus, the Env polypeptide comprising at least the amino acid residues K275, D276 and R278, wherein the numbering of said residues is according to the HxB2 reference sequence having the amino acid sequence of SEQ ID NO: 1.

In a preferred embodiment, the isolated, recombinant or synthetic polypeptide comprising an Env polypeptide of an HIV virus, wherein the Env polypeptide according to the invention comprises a deletion of at least 4, more preferably 5, 6 or 7 amino acids of the consecutive amino acid sequence RSNNSNK, which correspond to the residues R185f, S185g, N185h, N186, S187, N188 and K189 of the amino acid sequence of SEQ ID NO: 2, numbered relative to the HxB2 reference sequence (HxB2 numbering includes letters in case of insertions relative to HxB2, as described in Lucas et al., J Immunol 1998 161:3776-80 (1998). SEQ ID NO: 2 includes the unmodified segment with the residues RSNNSNK (SEQ ID NO:7). This sequence shows lower affinity for germline versions of bNAbs targeting the trimer-apex, such as PG9 when compared to the sequence lacking those residues (see table 1). The SEQ ID NO:2 also shows a similar affinity for the germline version of CH01, which is a different trimer-apex antibody. Lower affinity for germline antibody precursors negatively influences the activation capacity of B-cells and hence, compromises the initiation of bNAb lineages. Hence, the deletion of said at least 4, more preferably 5, 6 or 7 amino acids of the residues RSNNSNK, which correspond to the residues R185f, S185g, N185h, N186, S187, N188 and K189 numbered according to the reference SEQ ID NO:1, enhance the affinity for germline versions of bNAbs targeting the trimer-apex, such as PG9 and CH01. Preferably, the Env polypeptide is a SOSIP Env polypeptide, preferably having an amino acid sequence having SEQ ID NO: 2, 3, 4, 5, 100, 101, 102, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198 or 199 as disclosed in WO2017055522A1, wherein the numbering of said residues is according to the HxB2 reference sequence having the amino acid sequence of SEQ ID NO: 1.

Preferably, the isolated, recombinant or synthetic polypeptide comprising an Env polypeptide of an HIV virus, the Env polypeptide according to the invention, comprises at least 1, more preferably 2, 3 or 4 amino acid residues selected from the group consisting of: A199, D386, D462, and 5471, wherein the numbering of said residues is according to the HxB2 reference sequence having the amino acid sequence of SEQ ID NO: 1. The Env polypeptides having the amino acid sequence according to SEQ ID NO: 3, which includes the amino acid residues consisting of K275, D276 and R278 achieve broad binding antibody activity in the gl-VRC01-class measured by the binding activity of gl-12A12 and gl-3BNC60. In addition to those three residues, the incorporation of at least 1, more preferably 2, 3 or 4 amino acid residues consisting of: A199, D386, D462, and 5471, increases the affinity of gl-VRC01-class antibodies when compared to the sequence lacking those residues (FIG. 1 and Table 1).

In a preferred embodiment, the isolated, recombinant or synthetic polypeptide according to the invention, comprising at least 1, more preferably 2, 3, 4, 5, 6, 7, 8 or 9 amino acid residue(s) selected from the group consisting of: R169, H173, A174, K178, I181, P183, N188, T189, and S190, wherein the numbering of said residues is according to the HxB2 reference sequence having the amino acid sequence of SEQ ID NO: 1. The presence of these residues increases even more the affinity for the germline versions PG9 and CH01.

Preferably, the isolated, recombinant or synthetic polypeptide according to the invention, comprises at least 1, 2, 3, 4, 5 or 6 amino acid residue(s) selected from the group consisting of: R169, H173, A174, K178 I181 and P183, wherein the numbering of said residues is according to the HxB2 reference sequence having the amino acid sequence of SEQ ID NO: 1. The presence of residues R169, H173, A174, K178 I181 and P183, increases even more the affinity for the germline versions PG9 and CH01. Higher affinity for germline antibody precursors increases the efficiency of B-cell activation.

Preferably, the isolated, recombinant or synthetic polypeptide according to the invention, comprises at least 1, 2 or 3 amino acid residue(s) selected from the group consisting of: N188, T189, and S190, wherein the numbering of said residues is according to the HxB2 reference sequence having the amino acid sequence of SEQ ID NO: 1. The addition of the amino acid changes N188, T189, and S190, increases even more the affinity for the germline versions PG9 and CH01.

In a preferred embodiment, the isolated, recombinant or synthetic polypeptide according to any of the invention comprises at least 1 or 2 amino acid residue(s) selected from the group consisting of W316 and K64, wherein the numbering of said residues is according to the HxB2 reference sequence having the amino acid sequence of SEQ ID NO: 1. The advantage thereof is that these residues provide further stability to a trimer comprising said isolated, recombinant or synthetic polypeptide.

In a preferred embodiment, the Env polypeptide comprises:
 a gp120 polypeptide portion and at least a gp41 ectodomain polypeptide portion from HIV-1, or
 a gp125 polypeptide portion and at least a gp36 ectodomain polypeptide portion from HIV-2; wherein said gp120 or gp125 polypeptide portion comprises a first cysteine residue at an amino acid position equivalent to amino acid position 49, 50, 51, 71, 72 or 73, and wherein said gp41 or gp36 ectodomain polypeptide portion comprises a second cysteine residue at an amino acid position equivalent to an amino acid position selected from the group consisting of: 553, 554, 555, 556, 557, 558, 559, 560, 561, 562, 563, 564, 565, 566, 567, 568, 569 and 570, wherein said numbering is according to the HxB2 reference sequence having the amino acid sequence of SEQ ID NO: 1, and wherein said first and said second cysteine residues form a disulfide bond between said gp120 and said gp41 polypeptide portions, or between said gp125 and said gp36 polypeptide portions. An advantage thereof of is that trimers comprising the Env polypeptides having said first and second cysteine are more stable.

In a preferred embodiment, the isolated, recombinant or synthetic polypeptide according to the invention, said Env polypeptide is of HIV-1.

The invention further provides a trimer comprising the isolated, recombinant or synthetic polypeptide according to the invention.

The invention further provides a virus like particle (VPL), nanoparticle or pseudoparticle comprising the isolated, recombinant or synthetic polypeptide according to the invention or the trimer according to the invention.

The invention further provides a pharmaceutical composition comprising the isolated, recombinant or synthetic polypeptide according to the invention, or the trimer according to the invention, or the virus like particle, nanoparticle or pseudoparticle according to the invention, and a pharmaceutically acceptable carrier, excipient, or diluent, and optionally, an adjuvant. Preferably, said pharmaceutical composition is suitable for immunizing a subject.

The invention further provides the isolated, recombinant or synthetic polypeptide according to the invention, the trimer according to the invention, the virus like particle, nanoparticle or pseudoparticle according to the invention, or the pharmaceutical composition according to the invention for use in a medical treatment of a subject. Said treatment preferably comprises any treatment inhibiting, the onset or progression of HIV. In a preferred embodiment, said treatment is a prophylactic treatment for reducing the likelihood of a subject's becoming infected with HIV. Preferably said treatment comprises the step of administering a therapeutically effective amount of the isolated, recombinant or synthetic polypeptide according to the invention, the trimer according to the invention, the virus like particle, nanoparticle or pseudoparticle according to the invention, or the pharmaceutical composition according to the invention to said subject.

The isolated, recombinant or synthetic polypeptide according to the invention comprising all embodiments above mentioned (SEQ ID NO:3) has the following characteristics: in vitro binding of multiple gl-bNAbs targeting the CD4bs and the trimer-apex. When used as immunogen in animal experiments (as shown herein in a humanized mouse model), the Env protein of the invention showed a strong and specific anti-CD4bs or anti-trimer-apex activation capacity when compared to SEQ ID: 2. This supports the use of the isolated, recombinant or synthetic polypeptide according to the invention for use in the treatment of an HIV infection or for use in the prevention of an HIV infection.

The invention further provides the isolated, recombinant or synthetic polypeptide according to the invention, the trimer according to the invention, the virus like particle, nanoparticle or pseudoparticle according to the invention, or the pharmaceutical composition according to the invention, for use in the treatment of an HIV infection or for use in the prevention of an HIV infection.

The invention further provides a nucleic acid encoding the isolated, recombinant or synthetic polypeptide according to the invention.

The invention further provides a vector comprising the nucleic acid according to the invention.

The invention further provides an isolated or recombinant eukaryotic or prokaryotic host cell comprising the vector of the invention.

DETAILED DESCRIPTION

Definitions

"HIV" refers to the human immunodeficiency virus. HIV includes, without limitation, HIV-1 and HIV-2. The HIV-1 virus may represent any of the known major subtypes or clades (e.g., Classes A, B, C, D, E, F, G, J, and H) or outlying subtype (Group 0). Also encompassed are other HIV-1 subtypes or clades that may be isolated. There are two distinct types of HIV, HIV-1 and HIV-2, which are distinguished by their genomic organization and their evolution from other lentiviruses. Based on phylogenetic criteria (i.e., diversity due to evolution), HIV-1 can be grouped into three groups (M, N, and O). Group M is subdivided into 11 clades (A through K). HIV-2 can be divided into six distinct phylogenetic lineages (clades A through F) (Human Retroviruses and AIDS 1998: A compilation and analysis of nucleic acid and amino acid sequences (Los Alamos National Laboratory, Los Alamos, N M, 1998, http://hiv-web.lanl.gov).

The term "Env gene", as used herein, refers to the polynucleotide of the viral genome that encodes the envelope protein of HIV.

The related terms "Env polypeptide", "Env protein" or "envelope polypeptide" refers to a molecule derived from an HIV envelope protein. The HIV envelope glycoprotein complex (Env) is displayed on the surface of the virus and is the target of neutralizing antibodies. Two different proteins comprise the Env complex: The HIV-1 comprises gp120, the surface component, and gp41, the transmembrane component. The HIV-2 Env polypeptide comprises the Env gp125 subunit, which is highly homologous to gp120 of HIV-1 and the HIV-2 transmembrane subunit gp36, which is highly homologous to HIV-1 gp41. Each functional Env complex consists of three copies of each of these two proteins in a trimer of heterodimers. The glycoproteins are initially produced during virus infection as a polyprotein precursor, designated gp160. Cellular proteases cleave gp160 into the two subunits, gp120 and gp41, which remain non-covalently associated with each other in the Env complex. The gp140 is a modified gp160, that lacks the segments of gp41 that normally are imbedded in the viral membrane (transmembrane or TM segment) or in the interior of the virus or cell (cytoplasmic tail, CT).

The term "Env polypeptide" encompasses without limitation a gp140 envelope polypeptide, gp145 envelope and gp160 envelope polypeptide. Preferably, the Env polypeptide comprises a mature Env monomer.

As used herein, the term "mature Env monomer" refers to both a HIV-1 gp160 Env glycoprotein, comprising the HIV-1 Env gp120 subunit and the HIV-1 Env transmembrane subunit gp41, and to a HIV-2 gp140 glycoprotein, comprising the HIV-2 Env gp125 subunit and the HIV-2 transmembrane subunit gp36.

Preferably, said Env polypeptide comprises a soluble Env monomer. The term "soluble Env monomer" refers to both the soluble HIV-1 Env glycoprotein (termed gp140), comprising the HIV-1 Env gp120 subunit and the extracellular region of the HIV-1 Env gp41 subunit, and the soluble HIV-2 Env glycoprotein, comprising the HIV-2 Env gp125 subunit and the extracellular region of the HIV-2 Env gp36 subunit. The heterotrimeric nature of these HIV Env proteins are likely to result in the presentation of neutralization epitopes that differ from those on homotrimers, which may lead to the elicitation of broader neutralizing antibody responses upon immunization.

The term "gp140 envelope" or "gp140 envelope polypeptide" refers to a protein having two polypeptide chains, the first chain comprising the amino acid sequence of the HIV gp120 glycoprotein and the second chain comprising the amino acid sequence of the water-soluble portion of HIV gp41 glycoprotein ("gp41 portion"). HIV gp140 protein includes, without limitation, proteins wherein the gp41 portion comprises a point mutation such as T471S. A gp140 envelope comprising such mutation is encompassed by the terms "HIV SOS gp140", as well as "HIV gp140 monomer" or "SOSIP gp140".

The term "gp160 envelope" or "gp160 envelope polypeptide" refers to a protein having two polypeptide chains, the first chain comprising the amino acid sequence of the HIV gp120 glycoprotein and the second chain comprising the amino acid sequence of the complete (thus including the transmembrane portion of gp41) HIV gp41 glycoprotein ("gp41 portion").

The term "gp145 envelope" or "gp145 envelope polypeptide" refers to a protein having two polypeptide chains, the first chain comprising the amino acid sequence of the HIV gp120 glycoprotein and the second chain comprising the amino acid sequence of a truncated HIV gp41 glycoprotein ("gp41 portion"), wherein the cytoplasmic tail is deleted.

The term "gp41" includes, without limitation, (a) the entire gp41 polypeptide including the transmembrane and cytoplasmic domains (also referred herein as "complete polypeptide portion"); (b) gp41 ectodomain (gp41$_{ECTO}$); (c) gp41 comprising the ectodomain and the transmembrane domains, but without the cytoplasmic tail; (d) gp41 modified by deletion or insertion of one or more glycosylation sites; (e) gp41 modified so as to eliminate or mask the well-known immunodominant epitope; (f) a gp41 fusion protein; and (g) gp41 labeled with an affinity ligand or other detectable marker.

As used herein, "ectodomain" means the extracellular region of a transmembrane protein exclusive of the transmembrane spanning and cytoplasmic regions.

gp41 polypeptides or polypeptide portions also include "gp41-derived molecules", which encompasses analogs (non-protein organic molecules), derivatives (chemically functionalized protein molecules obtained starting with the disclosed protein sequences) or mimetics (three-dimensionally similar chemicals) of the native gp120 structure, as well as protein sequence variants (such as mutants, for example deletions, such as loop deletions, insertions or point mutation in any combination), genetic alleles, fusions proteins of gp41, or combinations thereof.

As used herein, "gp41 portion" encompasses any gp41 polypeptides as defined above, including consensus peptides, which are derived from the HR2 domain of gp41 from any HIV isolate. These peptides can include gp41 homologs that have at least one amino acid substitution, deletion or insertion.

The term "gp120" as used herein refers to an envelope protein from HIV-1. The envelope protein is initially synthesized as a longer precursor protein of 845-870 amino acids in size, designated as gp160. gp160 forms a homotrimer and undergoes glycosylation in the endoplasmic reticulum and within the Golgi apparatus. It is then cleaved by a cellular protease into gp120 and gp41. Gp41 contains a transmembrane domain and remains in a trimeric configuration; it interacts with gp120 in a non-covalent manner. gp120 contains most of the external, surface-exposed, domains of the envelope glycoprotein complex, and it is gp120 which binds both to the cellular CD4 receptor and to the cellular chemokine receptors (such as CCR5).

The mature gp120 wildtype polypeptides have about 500 amino acids in the primary sequence. gp120 is heavily N-glycosylated giving rise to an apparent molecular weight of 120 kD. Exemplary sequence of wt gp160 polypeptides are shown on GENBANK®, for example accession numbers AAB05604 and AAD12142 incorporated herein by reference in their entirety as available on Feb. 25, 2009.

The gp120 core has a unique molecular structure, which comprises two domains: an "inner" domain (which faces gp41) and an "outer" domain (which is mostly exposed on the surface of the oligomeric envelope glycoprotein complex). The two gp120 domains are separated by a "bridging sheet" that is not part of either domain. The gp120 core typically comprises 25 beta strands, 5 alpha helices, and 10 defined loop segments. The 10 defined loop segments include five conserved regions (C1-C5) and five regions of high variability (V1-V5).

As used herein, "gp120 polypeptide" or "gp120 polypeptide portion" encompasses peptides, including consensus peptides, which are derived from the HR2 domain of gp120 from any HIV isolate. These peptides can include gp120 homologs that have at least one amino acid substitution, deletions or insertions. In a preferred embodiment, the gp120 polypeptide has the amino acid sequence of the amino acids of 31-511 of HxB2 SEQ ID NO:1 or an amino acid sequence having sequence identity of at least 70% thereto, more preferably 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, wherein the positions are numbered according to the HxB2 reference sequence. In another preferred embodiment, said gp120 polypeptide or gp120 polypeptide portion refers to residues 31-511 of SEQ ID NO:1 or an amino acid sequence having sequence identity of at least 70% thereto, more preferably 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, wherein numbering is according to SEQ ID NO:1.

The HxB2 numbering is as described in Lucas et al., J Immunol 1998 161:3776-80 (1998) for an example and illustrated in the sequence alignment of SEQ ID NO:1, 2 and 3 as described herein. In case of insertion vis a vis the HxB2 reference sequence, the residue number/alphabet coding (e.g., R185f, S185g, N185h, etc.) is followed as described in Lucas et al. to refer to residues in variable regions that are "extra" compared to what HXB2 has. A similar scheme has been used for immunoglobulin complementarity-determining region (CDR) loops.

For example:
452, 465 and 470 are position relative to HXB2
452 465 470
| | |
LLLTRDGGNSNNES-EIFRP (SEQ ID NO: 8)
LLLTRDGGSNRSEPEVEIFRP (SEQ ID NO: 9)

Residues referred to as E465a and V465b correspond to HxB2 gp160 position numbers 452.

"Corresponding to", "reference to" or "relative to" when used in the context of the numbering of a given amino acid or polynucleotide sequence refers to the numbering of the residues of a specified reference sequence when the given amino acid or polynucleotide sequence is compared to the reference sequence. In other words, the residue number or residue position of a given polymer is designated with respect to the reference sequence rather than by the actual numerical position of the residue within the given amino acid or polynucleotide sequence. For example, a given amino acid sequence, such as that of an Env polypeptide, can be aligned to a reference sequence by introducing gaps to optimize residue matches between the two sequences. In these cases, although the gaps are present, the numbering of the residue in the given amino acid or polynucleotide sequence is made with respect to the reference sequence to which it has been aligned.

gp120 polypeptides and portions thereof also include "gp120-derived molecules" which encompasses analogs (non-protein organic molecules), derivatives (chemically functionalized protein molecules obtained starting with the disclosed protein sequences) or mimetics (three-dimensionally similar chemicals) of the native gp120 structure, as well as protein sequence variants (such as mutants, for example deletions, such as loop deletions, insertions or point mutation in any combination), genetic alleles, fusions proteins of gp120, or combinations thereof.

As used herein, a variant gp120 polypeptide is a gp120 polypeptide in which one or more amino acids have been altered (e.g., inserted, deleted or substituted). In one example, a variant gp120 polypeptide is a gp120 polypeptide in which at least 8 consecutive residues, such as 9, 10, 11 or 12 consecutive residues, of the fourth conserved loop (C4) between residues 419 and 434 of gp120 of SEQ ID NO:1 have been deleted. In a particular example, a variant gp120 polypeptide includes a gp120 polypeptide in which residues 424-432 are deleted. Additional variant gp120 polypeptides include deletions of INMWQKVGK (SEQ ID NO: 10, residues 434-442 of SEQ ID NO:1), INMWQKVGKA (SEQ ID NO: 11, residues 434-443 of SEQ ID NO:1), INMWQKVGKAM (SEQ ID NO: 12, residues 434-444 of SEQ ID NO:1), RIKQIINMWQKVGK (SEQ ID NO: 13, residues 429-442 of SEQ ID NO:1), IKQIINMWQKVGK (SEQ ID NO: 14, residues 430-442 of SEQ ID NO:1), KQIINMWQKVGK (SEQ ID NO: 15, residues 431-442 of SEQ ID NO:1), QIINMWQKVGK (SEQ ID NO: 16, residues 422-442 of SEQ ID NO:1), IINMWQKVGK (SEQ ID No:17, residues 433-442 of SEQ ID NO:1). In other embodiments, variant gp120 polypeptides include combinations of the amino and carboxyl ends between residues 429 and 444.

Any of the disclosed variant gp120 polypeptide including deletions in C4 can also include a deletion in the V1V2 loop region (with an amino acid sequence set forth in SEQ ID NO:1); see S R Pollard and DC Wiley, EMBO J. 11:585-91, 1992 which is hereby incorporated by reference in its entirety.

Unless the amino acid numbering of gp140/145/160/120/41/125/36 polypeptides disclosed herein is directly referred to a specific sequence, the numbering is relative to the HxB2 numbering scheme as shown for SEQ ID NO:1 in this application.

The term "fragment", as used herein, refers to a unique portion of the polynucleotide encoding the HIV-1 envelope polypeptide of the present invention shorter in length than the parent sequence. Similarly, the term "fragment" refers to an HIV-1 envelope polypeptide of the present invention comprising up to the entire length of the defined peptide sequence minus one amino acid residue and the coding nucleotide sequence thereof. For example, a fragment may comprise from 5 to 2500 contiguous nucleotides or amino acid residues. A fragment used as a probe, primer, antigen, therapeutic molecule, or for other purposes, may be at least 5, 10, 15, 16, 20, 25, 30, 40, 50, 60, 75, 100, 150, 250, 500, 550, or at least 600, 664 contiguous nucleotides or amino acid residues in length. Fragments may be preferentially selected from certain regions of a molecule. For example, a polypeptide fragment may comprise a certain length of contiguous amino acids selected from the first 250 or 500 amino acids (or first 25 percent or 50 percent) of a polypeptide as shown in a certain defined sequence. Clearly these lengths are exemplary, and any length that is supported by the specification, including the Sequence Listing, tables, and figures, may be encompassed by the present embodiments.

```
SEQ NO: 1 = HxB2; SEQ NO: 2 = BG505 SOSIP4.1; SEQ NO: 3 = Improved SOSIP4.1 Env protein:
BG505 SOSIP.v4.1-GT1.1
                              40         50         60         70
                    ....|....|....|....|....|....|....|....|.
SEQ ID NO: 1  ~~~~~MRVKEKYQHLWRWGWRWGTMLLGMLMICSATEKLWVTVYYGVPVWKEATTTLFCASDAKAYDTEVHNVWAT
SEQ ID NO: 2                               AENLWVTVYYGVPVWKDAETTLFCASDAKAYETKKHNVWAT
SEQ ID NO: 3                               AENLWVTVYYGVPVWKDAETTLFCASDAKAYETKKHNVWAT 80        90        100       110       120       130       140
   ...|....|....|....|....|....|....|....|....|....|....|... .|....|....|....|.
SEQ ID NO: 1  HACVPTDPNPQEVVLVNVTENFNMWKNDMVEQMHEDIISLWDQSLKPCVKLTPLCVSLKCTD~LKNDTNTNSSSGR
SEQ ID NO: 2  HACVPTDPNPQEIHLENVTEEFNMWKNNMVEQMHTDIISLWDQSLKPCVKLTPLCVTLQCTNVTNNIT~~~~~~~~
SEQ ID NO: 3  HACVPTDPNPQEIHLENVTEEFNMWKNNMVEQMHTDIISLWDQSLKPCVKLTPLCVTLQCTNVTNNIT~~~~~~~~
```

-continued

```
                  150       160       170       180              190       200       210
              ...|....|....|....|....|....|....|....|....      |....|....|....|....|....
SEQ ID NO: 1  MIMEKGEIKNCSFNISTSIRGKVQKEYAFFYKLDIIPIDNDTT~~~~~~~~SYKLTSCNTSVITQACPKVSFEPIP
SEQ ID NO: 2  ~DDMRGELKNCSFNMTTELRDKKQKVYSLFYRLDVVQINENQGNRSNNSNKEYRLINCNTSAITQACPKVSFEPIP
SEQ ID NO: 3  ~DDMRGELKNCSFNMTTELRDKRQKVHALFYKLDIVPINENQNT~~~~~~~SYRLINCNTAAITQACPKVSFEPIP 220       230       240       250       260       270       280
              |....|....|....|....|....|....|....|....|....|....|....|....|....|....|....
SEQ ID NO: 1  IHYCAPAGFAILKCNNKTFNGTGPCTNVSTVQCTHGIRPVVSTQLLLNGSLAEEEVVIRSVNFTDNAKTIIVQLN
SEQ ID NO: 2  IHYCAPAGFAILKCKDKKFNGTGPCPSVSTVQCTHGIKPVVSTQLLLNGSLAEEEVMIRSENITNNAKNILVQFN
SEQ ID NO: 3  IHYCAPAGFAILKCKDKKFNGTGPCPSVSTVQCTHGIKPVVSTQLLLNGSLAEEEVMIRSKDIRNNAKNILVQFN 290       300       310       320       330       340       350       360
              |....|....|....|....|....|....|....|... .|....|....|....|....|....|....|...
SEQ ID NO: 1  TSVEINCTRPNNNTRKRIRIQRGPGRAFVTIGKI~GNMRQAHCNISRAKWNNTLKQIASKLREQFGNNKTIIFKQ
SEQ ID NO: 2  TPVQINCTRPNNNTRKSIRI~~GPGQWFYATGDIIGDIRQAHCNVSKATWNETLGKVVKQLRKHFGNNTIIRFAN
SEQ ID NO: 3  TPVQINCTRPNNNTRKSIRI~~GPGQWFYATGDIIGDIRQAHCNVSKATWNETLGKVVKQLRKHFGNNTIIRFAN 370       380       390       400       410       420       430
              .|....|....|....|....|....|....|....|....|....|....|....|....|....|....|....
SEQ ID NO: 1  SSGGDPEIVTHSFNCGGEFFYCNSTQLFNSTWFNSTWSTEGSNNTEGSDTITLPCRIKQIINMWQKVGKAMYAPPI
SEQ ID NO: 2  SSGGDLEVTTHSFNCGGEFFYCNTSGLFNSTWISNTSVQ~GSNSTGSNDSITLPCRIKQIINMWQRIGQAMYAPPI
SEQ ID NO: 3  SSGGDLEVTTHSFNCGGEFFYCDTSGLFNSTWISNTSVQ~GSNSIGSNDSITLPCRIKQIINMWQRIGQAMYAPPI 440       450       460       470       480       490       500       510
              |....|....|....|....|....|....|....|.... .|....|....|....|....|....|....|.
SEQ ID NO: 1  SGQIRCSSNITGLLLTRDGGNSNN~ESEIFRPGGGDMRDNWRSELYKYKVVKIEPLGVAPTKAKRRVVQREKR~~A
SEQ ID NO: 2  QGVIRCVSNITGLILTRDGGSTNST~TETFRPGGGDMRDNWRSELYKYKVVKIEPLGVAPIRCKRRVVGRRRRRA
SEQ ID NO: 3  QGVIRCVSNITGLILTRDGGSTDST~TETFRPSGGDMRDNWRSELYKYKVVKIEPLGVAPTRCKRRVVGRRRRRA 520       530       540       550       560       570       580
              .|....|....|....|....|....|....|....|....|....|....|....|....|....|....|...
SEQ ID NO: 1  VGIGALFLGFLGAAGSTMGAASMTLTVQARQLLSGIVQQQNNLLRAIEAQQHLLQLTVWGIKQLQARILAVERYLK
SEQ ID NO: 2  VGIGAVFLGFLGAAGSTMGAASMTLTVQARNLLSGIVQQQSNLLRAPEAQQHLLKLTVWGIKQLQARVLAVERYLR
SEQ ID NO: 3  VGIGAVFLGFLGAAGSTMGAASMTLTVQARNLLSGIVQQQSNLLRAPEAQQHLLKLTVWGIKQLQARVLAVERYLR 590       600       610       620       630       640       650       660
              .|....|....|....|....|....|....|....|....|....|....|....|....|....|....|....
SEQ ID NO: 1  DQQLLGIWGCSGKLICTTAVPWNASWSNKSLEQIWNHTTWMEWDREINNYTSLIHSLIEESQNQQEKNEQELLELD
SEQ ID NO: 2  DQQLLGIWGCSGKLICCTNVPWNSSWSNRNLSEIWDNMTWLQWDKEISNYTQIIYGLLEESQNQQEKNEQDLLALD
SEQ ID NO: 3  DQQLLGIWGCSGKLICCTNVPWNSSWSNRNLSEIWDNMTWLQWDKEISNYTQIIYGLLEESQNQQEKNEQDLLALD
```

The term "truncated Env polypeptide" as used herein refers to a fragment of the Env polypeptide, which comprises at least a gp120 portion and an ectodomain portion of gp41.

As used herein, the terms "heptad repeat 1" and "HR1" are used indistinctly to refer to an heptad repeat region that is located at the amino terminus of wild-type gp41. A heptad repeat is a motif in which a hydrophobic amino acid is repeated every seven residues; such motifs are designated a through g. See Lupas A, Trends Biochem. Sci. 1996; 21:375-382. Heptad repeats which contain hydrophobic or neutral residues at the a and d positions can form alpha helices and are able to interact with other heptad repeats by forming coiled coils. See Chambers P, et al., J. Gen. Virol. 1990; 71:3075-3080; Lupas A, supra. The gp41 HR1 and HR2 sequences are well known in the art. See Miller M, et al., Proc. Natl. Acad. Sci. USA 2005; 102:14759-14764. In the particular case of the HxB2 env protein, the HR1 region corresponds to amino acids 542 to 591 of the polypeptide depicted in SEQ ID NO:1.

The term "pharmaceutically acceptable carriers" are well known to those skilled in the art and include, but are not limited to, 0.01-0.1M and preferably 0.05M phosphate buffer, phosphate-buffered saline (PBS), or 0.9% saline. Additionally, such pharmaceutically acceptable carriers may include, but are not limited to, aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers, diluents and excipients include water, alcoholic/aqueous solutions, emulsions or suspensions, saline and buffered media. Parenteral vehicles include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Solid compositions may comprise nontoxic solid carriers such as, for example, glucose, sucrose, mannitol, sorbitol, lactose, starch, magnesium stearate, cellulose or cellulose derivatives, sodium carbonate and magnesium carbonate. For administration in an aerosol, such as for pulmonary and/or intranasal delivery, an agent or composition is preferably formulated with a nontoxic surfactant, for example, esters or partial esters of C6 to C22 fatty acids or natural glycerides, and a propellant. Additional carriers such as lecithin may be included to facilitate intranasal delivery. Preservatives and other additives, such as, for example, antimicrobials, antioxidants, chelating agents, inert gases, and the like may also be included with all the above carriers.

Adjuvants are formulations and/or additives that are routinely combined with antigens to boost immune responses. Suitable adjuvants for nucleic acid based vaccines include, but are not limited to, saponins, Quil A, imiquimod, resiquimod, interleukin-12 delivered in purified protein or nucleic acid form, short bacterial immunostimulatory nucleotide sequences such as CpG-containing motifs, interleukin-2/Ig fusion proteins delivered in purified protein or nucleic acid form, oil in water micro-emulsions such as MF59, polymeric microparticles, cationic liposomes, monophosphoryl lipid A, immunomodulators such as Ubenimex, and genetically detoxified toxins such as *E. coli* heat labile toxin and cholera toxin from *Vibrio*. Such adjuvants and methods of combining adjuvants with antigens are well known to those skilled in the art.

Adjuvants suitable for use with protein immunization include, but are not limited to, alum; Freund's incomplete adjuvant (FIA); saponin; Quil A; QS-21; Ribi Detox; monophosphoryl lipid A (MPL) adjuvants such as Enhanzyn™; nonionic block copolymers such as L-121 (Pluronic; Syntex SAF); TiterMax Classic adjuvant (block copolymer, CRL89-41, squalene and microparticulate stabilizer; Sigma-Aldrich); TiterMax Gold Adjuvant (new block copolymer, CRL-8300, squalene and a sorbitan monooleate; Sigma-Aldrich); Ribi adjuvant system using one or more of the following: monophosphoryl lipid A, synthetic trehalose, dicorynomycolate, mycobacterial cell wall skeleton incorporated into squalene and polysorbate-80; Corixa); RC-552 (a small molecule synthetic adjuvant; Corixa); Montanide adjuvants (including Montanide IMSIIIX, Montanide IMS131x, Montanide IMS221x, Montanide IMS301x, Montanide ISA 26A, Montanide ISA206, Montanide ISA 207, Montanide ISA25, Montanide ISA27, Montanide ISA28, Montanide ISA35, Montanide ISA50V, Montanide ISA563, Montanide ISA70, Montanide ISA 708, Montanide ISA740, Montanide ISA763A, and Montanide ISA773; Seppic Inc., Fairfield, N.J.); and N-Acetylmuramyl-L-alanyl-D-isoglutamine hydrate (Sigma-Aldrich). Methods of combining adjuvants with antigens are well known to those skilled in the art.

Because current vaccines depend on generating antibody responses to injected antigens, commercially available adjuvants have been developed largely to enhance these antibody responses. To date, the only FDA-approved adjuvant for use with human vaccines is alum. However, although alum helps boost antibody responses to vaccine antigens, it does not enhance T cell immune responses. Thus, adjuvants that are able to boost T cell immune responses after a vaccine is administered are also contemplated for use. It is also known to those skilled in the art that cytotoxic T lymphocyte and other cellular immune responses are elicited when protein-based immunogens are formulated and administered with appropriate adjuvants, such as ISCOMs and micron-sized polymeric or metal oxide particles. Certain microbial products also act as adjuvants by activating macrophages, lymphocytes and other cells within the immune system, and thereby stimulating a cascade of cytokines that regulate immune responses. One such adjuvant is monophosphoryl lipid A (MPL), which is a derivative of the gram-negative bacterial lipid A molecule, one of the most potent immunostimulants known. The Enhanzyn™ adjuvant (Corixa Corporation, Hamilton, Mont.) consists of MPL, mycobacterial cell wall skeleton and squalene.

Adjuvants may be in particulate form. The antigen may be incorporated into biodegradable particles composed of polylactide-co-glycolide (PLG) or similar polymeric material. Such biodegradable particles are known to provide sustained release of the immunogen and thereby stimulate long-lasting immune responses to the immunogen. Other particulate adjuvants include, but are not limited to, micellular particles comprising Quillaia saponins, cholesterol and phospholipids known as immunostimulating complexes (ISCOMs; CSL Limited, Victoria AU), and superparamagnetic particles. Superparamagnetic microbeads include, but are not limited to, [mu]MACS™ Protein G and [mu]MACS™ Protein A microbeads (Miltenyi Biotec), Dynabeads® Protein G and Dynabeads® Protein A (Dynal Biotech). In addition to their adjuvant effect, superparamagnetic particles such as [mu] MACS™ Protein G and Dynabeads® Protein G have the important advantage of enabling immunopurification of proteins.

A "prophylactically effective amount" is any amount of an agent which, when administered to a subject prone to suffer from a disease or disorder, inhibits or prevents the onset of the disorder. The prophylactically effective amount will vary with the subject being treated, the condition to be treated, the agent delivered and the route of delivery. A person of ordinary skill in the art can perform routine titration experiments to determine such an amount. Depending upon the agent delivered, the prophylactically effective amount of agent can be delivered continuously, such as by continuous pump, or at periodic intervals (for example, on one or more separate occasions). Desired time intervals of multiple amounts of a particular agent can be determined without undue experimentation by one skilled in the art.

"Inhibiting" the onset of a disorder means either lessening the likelihood of the disorder's onset, preventing the onset of the disorder entirely, or in some cases, reducing the severity of the disease or disorder after onset. In the preferred embodiment, inhibiting the onset of a disorder means preventing its onset entirely.

"Reducing the likelihood of a subject's becoming infected with HIV" means reducing the likelihood of the subject's becoming infected with HIV by at least two-fold. For example, if a subject has a 1% chance of becoming infected with HIV, a twofold reduction in the likelihood of the subject becoming infected with HIV would result in the subject having a 0.5% chance of becoming infected with HIV. In the preferred embodiment of this invention, reducing the likelihood of the subject's becoming infected with HIV means reducing the likelihood of the subject's becoming infected with the virus by at least ten-fold.

"Subject" means any animal or artificially modified animal. Animals include, but are not limited to, humans, non-human primates, cows, horses, sheep, goats, pigs, dogs, cats, rabbits, ferrets, rodents such as mice, rats and guinea pigs, and birds and fowl, such as chickens and turkeys. Artificially modified animals include, but are not limited to, transgenic animals or SCID mice with human immune systems. In the preferred embodiment, the subject is a human.

"Exposed" to HIV means contact or association with HIV such that infection could result. A "therapeutically effective amount" is any amount of an agent which, when administered to a subject afflicted with a disorder against which the agent is effective, causes the subject to be treated. "Treating" a subject afflicted with a disorder shall mean causing the subject to experience a reduction, diminution, remission, suppression, or regression of the disorder and/or its symptoms. In one embodiment, recurrence of the disorder and/or its symptoms is prevented. Most preferably, the subject is cured of the disorder and/or its symptoms.

"HIV infected" means the introduction of viral components, virus particles, or viral genetic information into a cell, such as by fusion of cell membrane with HIV. The cell may be a cell of a subject. In the preferred embodiment, the cell is a cell in a human subject.

"Host cells" include, but are not limited to, prokaryotic cells, e.g., bacterial cells (including gram-positive cells), yeast cells, fungal cells, insect cells and animal cells. Suitable animal cells include, but are not limited to HeLa cells, COS cells, CVI cells and various primary mammalian cells. Numerous mammalian cells can be used as hosts, including, but not limited to, mouse embryonic fibroblast NIH-3T3 cells, CHO cells, HeLa cells, L(tk−) cells, PER.C6 and COS cells. Mammalian cells can be transfected by methods well known in the art, such as calcium phosphate precipitation, electroporation and microinjection. Electroporation can also be performed in vivo as described previously (see, e.g., U.S. Pat. Nos. 6,110,161; 6,262,281; and 6,610,044).

"Immunizing" means generating an immune response to an antigen in a subject. This can be accomplished, for example, by administering a primary dose of an antigen, e.g., a vaccine, to a subject, followed after a suitable period of time by one or more subsequent administrations of the antigen or vaccine, so as to generate in the subject an immune response against the antigen or vaccine. A suitable period of time between administrations of the antigen or vaccine may readily be determined by one skilled in the art, and is usually on the order of several weeks to months. Adjuvant may or may not be co-administered.

"Nucleic acid" refers to any nucleic acid or polynucleotide, including, without limitation, DNA, RNA and hybrids thereof. The nucleic acid bases that form nucleic acid molecules can be the bases A, C, T, G and U, as well as derivatives thereof. Derivatives of these bases are well known in the art and are exemplified in PCR Systems, Reagents and Consumables (Perkin-Elmer Catalogue 1996-1997, Roche Molecular Systems, Inc., Branchburg, N.J., USA).

A "vector" refers to any nucleic acid vector known in the art. Such vectors include, but are not limited to, plasmid vectors, cosmid vectors and bacteriophage vectors. For example, one class of vectors utilizes DNA elements which are derived from animal viruses such as animal papilloma virus, polyoma virus, adenovirus, vaccinia virus, baculovirus, retroviruses (RSV, MMTC or MoMLV), Semliki Forest virus or SV40 virus. The eukaryotic expression plasmid PPI4 and its derivatives are widely used in constructs described herein. However, the invention is not limited to derivatives of the PPI4 plasmid and may include other plasmids known to those skilled in the art. In accordance with the invention, numerous vector systems for expression of recombinant proteins may be employed. For example, one class of vectors utilizes DNA elements which are derived from animal viruses such as bovine papilloma virus, polyoma virus, adenovirus, vaccinia virus, baculovirus, retroviruses (RSV, MMTV or MoMLV), Semliki Forest virus or SV40 virus. Additionally, cells which have stably integrated the DNA into their chromosomes may be selected by introducing one or more markers which allow for the selection of transfected host cells. The marker may provide, for example, prototropy to an auxotrophic host, biocide (e.g., antibiotic) resistance, or resistance to heavy metals such as copper or the like. The selectable marker gene can be either directly linked to the DNA sequences to be expressed, or introduced into the same cell by cotransformation. Additional elements may also be needed for optimal synthesis of mRNA. These elements may include splice signals, as well as transcriptional promoters, enhancers, and termination signals. The cDNA expression vectors incorporating such elements include those described by (Okayama and Berg, 1983).

The term "Protein conformation" refers to the characteristic 3-dimensional shape of a protein, including the secondary (helices, sheet), supersecondary (motifs), tertiary (domains) and quaternary (multimeric proteins) structure of the peptide chain.

The term "native conformation" as used herein refers to the characteristic state, formation, shape or structure of a protein in the biologically active form in a living system in which it is folded to a global minimum of Gibbs free energy as defined by C. B. Anfinsen (Nobel Lecture, Dec. 11, 1972).

The methods described above are used preferably for the isolation of recombinantly produced proteins in the native conformation. Recombinantly produced proteins can be either directly expressed or expressed as a fusion protein. Detection of the expressed protein is achieved by methods known in the art such as, for instance, radioimmunoassays, Western blotting techniques or immunoprecipitation.

Based on loop-movement, compactness and angles between individual protomers, the Env trimers may be classified as closed native-like, partially open native-like or non-native (Pugach et al., 2015). Native-like trimers are regularly shaped and have the highest concentration of electron density at the particle center (usually shaped like a triangle because Env is trimeric). The absence or presence of additional density around this center of mass determines whether trimers are classified as closed native-like or partially open native-like, respectively. Non-native forms are often elongated and no triangular center of density is visible.

The term "closed native conformation" or "closed conformation" when referring to an Env trimer, refers to the visual shape of the Env trimer as previously described for BG505 SOSIP.664 (Sander et al. 2013, A next-generation cleaved, soluble HIV-1 Env trimer, BG505 SOSIP. 664 gp140, expresses multiple epitopes for broadly neutralizing but not non-neutralizing antibodies. PLoS Pathog 9:e1003618). Based on visual inspection of 2D images, an Env trimer has a closed native conformation if it has a compact triangular propeller shape with no additional density surrounding the trimer. Trimers containing triangular propeller density of an intensity and size similar to the closed native conformation group, but displaying one, two, or three smaller spheres of density at the distal ends of the triangular density, are defined as having an open native conformation.

The term "nonnative conformation" refers to the visual shape of an Env trimer particle which does not clearly show a central, triangular mass. Typically, a trimer having a nonnative conformation resembles previously described images of uncleaved, non-SOSIP gp140 proteins (Ringe R P et al. 2013. Cleavage strongly influences whether soluble HIV-1 envelope glycoprotein trimers adopt a native-like conformation. Proc Natl Acad Sci USA 110:18256-18261.

The conformation as described above of the isolated, recombinant or synthetic Env protein may suitably be characterized by negative stain electron microscopy (EM) and Reducing SDS-PAGE as described herein.

EMBODIMENTS OF THE INVENTION

The isolated, recombinant or synthetic Env proteins of the invention may be made of any Env polypeptide and may be of any type or clade of HIV. The HIV-1 Env polypeptide comprises a gp120 polypeptide portion and at least a gp41 ectodomain polypeptide portion. The present invention encompasses HIV envelope (Env) glycoprotein complexes, which comprise covalently associated surface gp120 and transmembrane gp41 glycoprotein subunits, and soluble forms thereof.

The gp41 portion encompasses any gp41 polypeptides or fragments or truncated forms thereof, including consensus peptides, which are derived from the HR2 domain of gp41 from any HIV isolate. These peptides can include gp41 homologs that have at least one amino acid substitution, deletions or insertions.

Gp41 polypeptides or polypeptide portions also include "gp41-derived molecules" which encompasses analogs (non-protein organic molecules), derivatives (chemically functionalized protein molecules obtained starting with the disclosed protein sequences) or mimetics (three-dimensionally similar chemicals) of the native gp120 structure, as well as proteins sequence variants (such as mutants, for example deletions, such as loop deletions, insertions or point mutation in any combination), genetic alleles, fusions proteins of gp41, or combinations thereof.

In a preferred embodiment, the gp41 ectodomain polypeptide portion has the amino acid sequence of the amino acids of positions 512-664 of HxB2 SEQ ID NO:1 or an amino acid sequence having sequence identity of at least 70% thereto, more preferably 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

In another preferred embodiment, said gp41 ectodomain polypeptide portion refers to residues 516-664 SEQ ID NO:1 or an amino acid sequence having sequence identity of at least 70% thereto, more preferably 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

The "gp120 polypeptide" or "gp120 polypeptide portion" encompasses peptides, including consensus peptides, which are derived from gp120 from any HIV isolate. These peptides can include gp120 homologs that have at least one amino acid substitution, deletions or insertions. In a preferred embodiment, the gp120 polypeptide has the amino acid sequence of the amino acids 31-511 of HxB2 SEQ ID NO:1 or an amino acid sequence having sequence identity of at least 70% thereto, more preferably 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, wherein the positions are numbered according to the HxB2 reference sequence.

It will be appreciated that once a certain amino acid is identified in, for example, a given gp160 sequence, the corresponding position in the gp160 sequence of other HIV-1 or HIV-2 isolates can be easily identified by aligning the sequence of both gp160 variants or by performing multiple alignment of the gp160 wherein the position of the disulfide bond is to be identified within a plurality of other gp160 sequences.

For sequence comparison, typically one sequence acts as a reference, to which the test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of HIV envelope glycoproteins, fusion proteins comprising envelope glycoproteins and nucleic acid sequences encoding the same, the BLAST and BLAST 2.0 algorithms and the default parameters discussed below are used.

The Env polypeptides according to the invention also encompass HIV-2 Env polypeptides. HIV-2 Env proteins comprise a gp125 polypeptide portion and at least a gp36 ectodomain polypeptide portion.

In another preferred embodiment, the isolated, recombinant or synthetic polypeptide is capable of forming homotrimers, preferably also of heterodimers.

In a preferred embodiment, the isolated, recombinant or synthetic Env protein of the invention has at least a homology of 70% to SEQ ID NO:1, more preferably 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

In another preferred embodiment, the isolated, recombinant or synthetic Env protein of the invention has at least a homology of 70% to SEQ ID NO:2, more preferably 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

In another preferred embodiment, the isolated, recombinant or synthetic Env protein of the invention has at least a homology of 70% to SEQ ID NO:3, more preferably 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

It is understood in the art that in order to make functionally equivalent amino acid substitutions, the hydropathic index of amino acids may be considered. The importance of the hydropathic amino acid index in conferring interactive biological function on a polypeptide is generally understood in the art. See Kyte J, Doolittle R, J. Mol. Biol. 1982; 15(1):105-132. It is known that certain amino acids may be substituted for other amino acids having a similar hydropathic index or score and still retain a similar biological activity. In making changes based upon the hydropathic index, the substitution of amino acids whose hydropathic indices are within plus or minus 2 is preferred, those which are within plus or minus 1 are particularly preferred, and those within plus or minus 0.5 are even more particularly preferred. Each amino acid has been assigned a hydropathic index on the basis of its hydrophobicity and charge characteristics; these are: isoleucine (+4.5), valine (+4.2), leucine (+3.8), phenylalanine (+2.8), cysteine/cystine (+2.5), methionine (+1.9), alanine (+1.8), glycine (−0.4), threonine (−0.7), serine (−0.8), tryptophan (−0.9), tyrosine (−1.3), proline (−1.6), histidine (−3.2), glutamate (−3.5), glutamine (−3.5), aspartate (−3.5), asparagine (−3.5), lysine (−3.9) and arginine (−4.5).

It also is understood in the art that the substitution of similar amino acids can be made effectively on the basis of hydrophilicity; particularly where the immunologically functional equivalent polypeptide thereby created is intended for use in immunological embodiments, as in certain embodiments of the present invention. The greatest local average hydrophilicity of a protein, as governed by the hydrophilicity of its adjacent amino acids, correlates with its immunogenicity and antigenicity. See Hopp T, U.S. Pat. No. 4,554,101. In making changes based upon similar hydrophilicity values, the substitution of amino acids whose hydrophilicity values are within plus or minus 2 is preferred, those which are within plus or minus 1 are particularly preferred, and those within plus or minus 0.5 are even more particularly preferred. The following hydrophilicity values have been assigned to amino acid residues: arginine (+3.0), lysine (+3.0), aspartate (+3.0 plus or minus 1), glutamate (+3.0 plus or minus 1), serine (+0.3), asparagine (+0.2), glutamine (+0.2), glycine (0), threonine (−0.4), proline (−0.5 plus or minus 1), alanine (−0.5), histidine (−0.5), cysteine (−1.0), methionine (−1.3), valine (−1.5), leucine (−1.8), isoleucine (−1.8), tyrosine (−2.3), phenylalanine (−2.5) and tryptophan (−3.4).

It is well known in the art that where certain residues are shown to be particularly important to the immunological or structural properties of a protein or peptide, like for example, residues in binding regions or epitopes, such residues may not generally be exchanged. In this manner, functional equivalents are defined herein as those polypeptides, which maintain a substantial amount of their native immunological activity. In general, the shorter the length of the molecule, the fewer changes can be made to the molecule without affecting its function. Longer domains may have an intermediate number of changes. The full-length protein will have the most tolerance for a larger number of changes. However, it must be appreciated that certain molecules or domains that are highly dependent upon their structure may tolerate little or no modification.

Env Trimers and VLPs

In an embodiment, the invention encompasses envelope trimers for the production of virus like particles (VPLs) and pseudoparticles for use as VLP-based immunogens, to generate neutralizing antibodies, for example, and VLP-based vaccines against which a subject can mount a potent immune response against HIV. In accordance with the invention, Env trimers comprising the amino acid residues of the invention, as well as Env trimers comprising other mutations in gp120 and gp41 or equivalents thereof from HIV-2 as described herein, are used to generate VPLs and pseudovirions having reduced monomer, dimer and tetramer forms and enhanced trimer forms of gp120/gp41 Env. The amino acid residues in the context of HIV-1 virus as described herein can yield trimer forms of Env (gp120/gp41) on VLP and pseudovirions, to the virtual exclusion of monomer, dimer and tetramer forms, thus allowing for an immunogen that more closely resembles native HIV envelope trimers.

Pharmaceutical Compositions

This invention provides a composition comprising the modified polypeptide of the invention and a pharmaceutically acceptable carrier, excipient, or diluent. This invention also provides a composition comprising the trimeric complex of the invention and a pharmaceutically acceptable carrier, excipient, or diluent. In one embodiment, the composition further comprises an adjuvant. In one embodiment, the composition further comprises an antiretroviral agent.

Compositions and immunogenic preparations, including vaccine compositions, comprising the polypeptides of the present invention capable of inducing an immunological reaction (including protective immunity) in a suitably treated animal or human, and a suitable carrier therefore, are provided. Immunogenic compositions are those which result in specific antibody production or in cellular immunity when injected into a human or an animal. Such immunogenic compositions or vaccines are useful, for example, in immunizing an animal, including a human, against infection and/or damage caused by HIV.

The vaccine preparations comprise an immunogenic amount of one or more of the isolated, recombinant or synthetic polypeptides of the invention. By "immunogenic amount" is meant an amount capable of eliciting the production of antibodies directed against the retrovirus in a mammal into which the vaccine has been administered. The route of administration and the immunogenic composition may be designed to optimize the immune response on mucosal surfaces, for example, using nasal administration (via an aerosol) of the immunogenic composition. In some embodiments, the methods and compositions of the invention also include use of another antiviral agent in addition to the one or more of the present Env polypeptides, or a combination of Env polypeptides as described herein. Thus, other antiretroviral agents or compounds, which can be administered in addition to the polypeptides and compositions of the invention include, without limitation, protease inhibitors, retroviral polymerase inhibitors, azidothymidine (AZT), didanoside (DDI), soluble CD4, a polysaccharide sulfates, T22, bicyclam, suramin, antisense oligonucleotides, ribozymes, rev inhibitors, protease inhibitors, glycolation inhibitors, interferon and the like. Examples include acyclovir, 3-aminopyridine-2-carboxyaldehyde thiosemicarbazone (3-AP, Triapine™) and 3-amino-4-methylpyridine-2-carboxaldehyde thiosemicarbazone (3-AMP), thiamine disulfide, thiamine disulfide nitrate, thiamine disulfide phosphate, bisbentiamine, bisbutytiamine, bisibutiamine, alitiamine, fursultiamine and octotiamine.

In a preferred embodiment, the pharmaceutical composition comprises a cocktail of different Env polypeptides. Preferably, said pharmaceutical composition comprises at least 2 different Env polypeptides. Preferably said pharmaceutical composition comprises at least 2, 3 or 4 different Env polypeptides according to the invention. An advantage thereof is that these compositions induce better heterologous responses against several Tier-2 viruses. Preferably, said pharmaceutical composition comprises at least 2, 3 or 4 different Env polypeptides of the invention.

Nanoparticles

The present invention provides novel Env-ferritin nanoparticle (np) vaccines. Such nanoparticles comprise fusion proteins, each of which comprises a monomeric subunit of ferritin joined to an immunogenic portion of an Env protein. Because such nanoparticles display Env protein on their surface, they can be used to vaccinate an individual against HIV.

In some embodiments of the present invention, the various protein domains (e.g., gp140 protein, trimerization domain, etc.) may be joined directly to one another. In other embodiments, it may be necessary to employ linkers (also referred to as a spacer sequences) so that the various domains are in the proper special orientation. The linker sequence is designed to position the Env protein in such a way to that it maintains the ability to elicit an immune response to the HIV virus. Linker sequences of the present invention comprise amino acids. Preferable amino acids to use are those having small side chains and/or those which are not charged. Such amino acids are less likely to interfere with proper folding and activity of the fusion protein. Accordingly, preferred amino acids to use in linker sequences, either alone or in combination are serine, glycine and alanine. Examples of such linker sequences include, but are not limited to, SGG, GSG, GG and NGTGGSG (SEQ ID. NO:18). Amino acids can be added or subtracted as needed. Those skilled in the art are capable of determining appropriate linker sequences for proteins of the present invention.

Methods of Treatment

Env polypeptides according to the invention and trimers thereof are useful components of vaccines aimed at inducing bNAbs. This invention also provides a method for preventing a subject from becoming infected with HIV, comprising administering to the subject an amount of the composition of the invention effective to prevent the subject from becoming infected with HIV. This invention further provides a method for reducing the likelihood of a subject becoming infected with HIV, comprising administering to the subject an amount of the composition of the invention effective to reduce the likelihood of the subject becoming infected with HIV.

This invention also provides a method for delaying the onset of, or slowing the rate of progression of, an HIV-related disease in an HIV-infected subject, which comprises administering to the subject an amount of the composition of the invention effective to delay the onset of, or slow the rate of progression of, the HIV-related disease in the subject.

This invention also provides a method for eliciting an immune response against HIV or an HIV infected cell in a subject comprising administering to the subject an amount of the composition of the invention effective to elicit the immune response in the subject. This invention provides a method for eliciting an immune response against HIV or an HIV infected cell in a subject comprising administering to the subject an amount of the trimeric complex of the invention effective to elicit the immune response in the subject.

EXAMPLE

Env Trimer Design and Mutagenesis

To generate the SEQ ID NO: 3, 18 individual point substitutions and a 7 amino-acid deletion (RSNNSNK) were introduced into the sequence BG505 SOSIP.664 (Sanders R W et al., PLoS Pathog. 2013 September; 9(9):e1003618. doi: 10.1371/journal.ppat.1003618. Epub 2013 Sep. 19). To generate variants of the BG505 SOSIP.664 with only one or a subset of the total number of substitution, the changes were introduced singly or in combination (i.e. N276D; or N276D+T278R; or E275K+N276D+T278R) into the variant BG505 SOSIP.v4.1 (SEQ ID NO: 2). To generate a variant of the SEQ ID NO: 2 with a 7 amino-acid deletion (RSNNSNK), mutagenesis primers (forward primer: SEQ ID NO:4 atcaatgaaaaccaggggaatgagtacaggctgatcaattg; reverse primer: SEQ ID NO:5 caattgatcagcctgtactcat-tccctggttttcattgat) were designed to match with the sequences flanking the RSNNSNK sequence of the SEQ ID NO: 2. All mutations were introduced using the QuikChange site-directed mutagenesis kit (Agilent, Stratagene, Santa Clara, Calif.) following the manufacturer's protocol. The primers for site directed mutagenesis were designed using the Agilent primer design online tool (http://www.genomics.agilent.com/primerDesignProgram.isp).

Expression and Purification of Recombinant Env Trimers of the HIV Virus

All variants of BG505 SOSIP.664 trimers were generated with a stop codon after the residue 664 when used for immunizations, or bearing a His-tag sequence (8 histidines) by adding the amino acid sequence GSGSGGSGHHHHHHHH (SEQ ID NO:6) after the residue 664 at the C-terminus of the gp41 ectodomain and preceding the stop codon when produced for binding assays. The presence or absence of these epitope tag does not influence the structure or antigenicity of the trimer. Expression vectors of recombinant Env trimers (i.e. SEQ ID NO: 3 or BG505 SOSIP.664 variants) were expressed by transient transfection of adherent HEK293T cells or the FreeStyle 293F variant (Invitrogen) that is adapted for suspension cultures as described in Sanders R W et al., PLoS Pathog. 2013 September; 9(9):e1003618. doi: 10.1371/journal.ppat.1003618. Epub 2013 Sep. 19. Env trimers were purified from culture supernatants by PGT145-affinity chromatography (De Taeye et al., Cell. 2015 Dec. 17; 163(7):1702-1715). Trimer cleavage and purity was assessed using SDS-PAGE and BN-PAGE analyses as described in Sanders et al., 2013

ELISA for Trimer Antigenicity

An ELISA protocol was adapted from described elsewhere (Derking et al., 2015). In brief, His-tagged Env trimers, either pure (3.5 µg/ml in TBS buffer) or in unpurified HEK293T cell culture supernatant, were immobilized (100 µl/well) for 2 h on 96-well Ni-NTA ELISA plates (QIA GEN). After washing away excess protein with Tris-buffered saline (TBS), the wells were blocked for 30 min with casein/TBS (37532; Thermo Fisher Scientific). Serial dilutions of each antibody were prepared in casein/TBS at a starting concentration of 1 µg/ml and added to the plate (100 µl/well; for lower affinity antibodies, the starting concentration was 50 µg/ml). The dilution factor for all antibodies was 1:3. Excess antibody was washed away after 2 h and antihuman HRP-conjugated antibody (diluted in casein/TBS 1:3,000) added for 45 min before binding was quantified. All steps were performed at room temperature.

Mice and Immunizations

The efficacy of both sequences SEQ ID NO:2 and SEQ ID NO:3 for use in prevention of an HIV infection was tested in vivo in two different mouse models engineered to express human anti-HIV bNAb precursors: 1) germline-like CH01 antibodies (targeting the trimer-apex); and 2) VRC01-like antibodies (targeting the CD4bs). The germline CH01 mouse model that expresses germline-like CH01 antibodies (carrying the Ig V[D]J genes encoding the germline sequence of the heavy chain of germline CH01) was produced targeting embryonic stem cells from laboratory-bred strains of house mouse (*Mus musculus*) (personal communication, Laurent K. Verkoczy, the Duke Human Vaccine Institute, Durham, N.C.). The VRC01$V_H V_L$ Rag2 chimera mouse model that expresses germline VRC01-like antibodies (IGHV1-2*02 in association with diverse CDR3s [complementarity-determining region 3]) was produced as described in Tian et al. (Cell. 2016 Sep. 8; 166(6):1471-1484). One and two independent experiments were performed using the germline CH01 mice and VRC01$V_H V_L$ Rag2 chimera mice, respectively. Mice were immunized two times every 2-4 wk intraperitoneally with 25 µg protein (SEQ ID NO:2 or SEQ ID NO:3) in Polyinosinic-polycytidylic acid (Poly(I:C)) adjuvant (InvivoGen). Serum samples were collected 2 wk after each immunization. All immunization and serum sample collection procedures were carried out in accordance with Institutional Animal Care and Use Committee and the Duke University Institutional Biosafety Committee—approved animal protocols.

ELISA for Antitrimer Antibodies in Mouse Sera

ELISAs to measure serum responses to the SEQ ID NO:2 or SEQ ID NO:3 were adapted from elsewhere (Yasmeen et al., 2014; Derking et al., 2015; Dosenovic et al., 2015). In brief, His-tagged antigen was captured by using Ni-NTA ELISA plates (QIA GEN) at 3.5 µg/ml in TBS to all the wells and incubated at room temperature for 2 h. Plates were then washed and blocked for 30 minutes at room temperature with 2% skim milk in TBS. After blocking, serum samples were added in 2% skim milk in TBS supplemented with 20% sheep serum (Biotrading) and incubated for 2 h at room temperature. Sera were added at 1:100 starting dilution. Seven additional threefold serial dilutions were made. Plates were washed and incubated for 30 minutes at room temperature with an HRP-antimouse IgG antibody (The Jackson Laboratory; in 2% skim milk in TBS) at a 1:3,000 dilution. Plates were developed by addition of the HRP substrate, ABTS (Thermo Fisher Scientific), and absorbance was measured with an ELISA microplate reader (at 450 nm in a Spectrostar nano, BMG Labtech).

TABLE 1

| Mutation | Function |
|---|---|
| E64K | Stabilization by reduction of CD4-induced epitopes |
| A316W | Stabilization by reduction of V3 loop exposure |
| K169R | Enhancement of electrostatic interaction with TyrH100G of PG9[b] |
| Y173H | H-bond with TyrH100K of PG9[b] |
| Q183P | Potential V2 stabilization by loss of conformational entropy |
| ΔRSNNSNK[a] | Potential V2 stabilization by reduction of flexibility |
| S199A | Removal of a N-glycan that clashes with the HCDR2 of V1-2*02 |
| E275K | Induction of one H-bond with HCDR3 of gl-VRC01-class bNAbs |

TABLE 1-continued

| Mutation | Function |
|---|---|
| N276D | Removal of a N-glycan that clashes with LCDR3 of VRC01-class antibodies |
| T278R | Induction of one H-bond with residue $S^{L28}$ of KV3-11*01 |
| N386D | Removal of a N-glycan with undetermined mechanism |
| N462D | Removal of a N-glycan that clashes with FR1 of KV3-11*01 |
| G471S | Induction of an extra H-bond within loop D |

[a]Deletion of seven amino acids corresponding to the residues R185f, S185g, N185h, N186, S187, N188 and K189 (HxB2 numbering) of the sequence of BG505.W6M.ENV.C2 (GenBank DQ208458.1)
[b]in silico modeled interaction.

The invention claimed is:

1. An isolated, recombinant or synthetic polypeptide comprising an Env polypeptide of an HIV virus, wherein said Env polypeptide comprises at least the amino acid residues K275, D276 and R278, wherein the numbering is according to the HxB2 reference sequence having the amino acid sequence of SEQ ID NO: 1.

2. The isolated, recombinant or synthetic polypeptide according to claim 1, not comprising at least 4, 5, 6 or 7 amino acids of the consecutive amino acid stretch RSNNSNK of the amino acid sequence of SEQ ID NO: 2, wherein the numbering is according to the HxB2 reference sequence having the amino acid sequence of SEQ ID NO: 1.

3. The isolated, recombinant or synthetic polypeptide according to claim 1, comprising at least one amino acid residue selected from the group consisting of: A199, D386, D462, and S471, wherein the numbering is according to the HxB2 reference sequence having the amino acid sequence of SEQ ID NO: 1.

4. The isolated, recombinant or synthetic polypeptide according to claim 1, comprising at least 1, more preferably 2, 3, 4, 5, 6, 7, 8 or 9 amino acid residue(s) selected from the group consisting of: R169, H173, A174, K178, I181, P183, N188, T189, and S190, wherein the numbering is according to the HxB2 reference sequence having the amino acid sequence of SEQ ID NO: 1.

5. The isolated, recombinant or synthetic polypeptide according to claim 1, wherein said Env protein has an amino acid sequence having at least 70% sequence identity to SEQ ID NO: 2.

6. The isolated, recombinant or synthetic polypeptide according to claim 1, comprising at least one amino acid residue selected from the group consisting of W316 and K64, wherein the numbering is according to the HxB2 reference sequence having the amino acid sequence of SEQ ID NO: 1.

7. The isolated, recombinant or synthetic polypeptide according to claim 1, wherein said Env polypeptide is of HIV-1.

8. A trimer comprising the isolated, recombinant or synthetic polypeptide according to claim 1.

9. A virus like particle (VPL), nanoparticle or pseudoparticle comprising the isolated, recombinant or synthetic polypeptide according to claim 1 or the trimer according to claim 8.

10. A pharmaceutical composition comprising the isolated, recombinant or synthetic polypeptide according to claim 1, or the trimer according to claim 8, or the virus like particle, nanoparticle or pseudoparticle according to claim 9, and a pharmaceutically acceptable carrier, excipient, or diluent, and optionally, an adjuvant.

11. The isolated, recombinant or synthetic polypeptide according to claim 1, or the trimer according to claim 8, or the virus like particle, nanoparticle or pseudoparticle according to claim 9, or the pharmaceutical composition according to claim 10 for use in a medical treatment.

12. The isolated, recombinant or synthetic polypeptide according to claim 1, or the trimer according to claim 8, or the virus like particle, nanoparticle or pseudoparticle according to claim 9, or the pharmaceutical composition according to claim 10 for use in the treatment of an HIV infection or for use in the prevention of an HIV infection.

13. A nucleic acid encoding the isolated, recombinant or synthetic polypeptide according to claim 1.

14. A vector comprising the nucleic acid according to claim 13.

15. An isolated or recombinant eukaryotic or prokaryotic host cell comprising the vector of claim 14.

* * * * *